United States Patent
Huang et al.

(10) Patent No.: US 7,422,853 B1
(45) Date of Patent: Sep. 9, 2008

(54) RNA INTERFERENCE USING A UNIVERSAL TARGET

(75) Inventors: Liwen Huang, Sandy, UT (US); Herbert L. Ley, III, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 438 days.

(21) Appl. No.: 10/680,449

(22) Filed: Oct. 6, 2003

Related U.S. Application Data

(60) Provisional application No. 60/416,353, filed on Oct. 4, 2002.

(51) Int. Cl.
  *C12Q 1/68* (2006.01)
  *C07H 21/04* (2006.01)

(52) U.S. Cl. .......................... 435/6; 536/24.5

(58) Field of Classification Search .................. None
See application file for complete search history.

(56) References Cited

U.S. PATENT DOCUMENTS

| | | | |
|---|---|---|---|
| 6,544,790 | B1 | 4/2003 | Sabatini |
| 2003/0036197 | A1 | 2/2003 | Glassman et al. |
| 2003/0068821 | A1 | 4/2003 | Lois-Caballe et al. |
| 2003/0139363 | A1 | 7/2003 | Kay et al. |
| 2003/0143597 | A1 | 7/2003 | Finney et al. |
| 2003/0144232 | A1 | 7/2003 | Agami et al. |
| 2003/0144239 | A1 | 7/2003 | Agami et al. |
| 2003/0150017 | A1 | 8/2003 | Mesa et al. |
| 2003/0167490 | A1 | 9/2003 | Hunter et al. |
| 2003/0224432 | A1* | 12/2003 | Myers et al. ............. 435/6 |
| 2004/0029275 | A1* | 2/2004 | Brown et al. ............. 435/375 |
| 2004/0203145 | A1 | 10/2004 | Zamore et al. |
| 2004/0224405 | A1 | 11/2004 | Leake et al. |
| 2004/0259247 | A1* | 12/2004 | Tuschl et al. ............. 435/375 |

OTHER PUBLICATIONS

Hirashima et al. (1986) PNAS 83:7726-7730.*
Cox et al. (1998) Genes & Development 12:3715-3727.*
Holen et al. [2002] Nucleic Acids Res. 30:1757-1766.*
Sijen et al. (2001) Cell 107:465-476.*
Fire et al. (1990) Gene 93:189-198.*
Kennerdell et al. (1998) Cell 95:1017-1026.*
Elbashir et al. (2001) Nature 411:494-498.*
Pal-Bhadra et al. (1998) Cell 99: 35-46.*
Voinnet et al. (1998) Cell 95:177-187.*
Barr, 1998, Nature Genetics 19:121-124.*
Reddy et al., 1999 TINS 22:248-255.*
Mullins et al. (1996) J. Clin. Invest. 98(11), Supplement S37-S40.*
Bradley et al. (1992) Biotechnology 10: 534-539.*
Doetschmann (1999) Lab. Animal Sci., vol. 49 (2), 137-143.*
Moens et al. (1993) Development, vol. 199, 485-499.*
Jacks et al. (1992) Nature, vol. 359, 295-300.*
Hannon, 2002, Nature 418:244-251.*

Alder et al., "Gene Silencing in *Caenorhabditis elegans* by transitive RNA interference," *RNA*, 2003, 9:25-32.
Bargmann, "High Throughput Reverse Genetics: RNAi Screen in *Caenorhabditis elegans*," *Genome Biology*, Jan. 31, 2001, 2(2):reviews 1005.1-1005.3.
Boutla et al., "Induction of RNA interference in *Caenorhabditis elegans* by RNAs derived from plants exhibiting post-transcriptional gene silencing," *Nucleic Acids Research*, Feb. 4, 2002, 30(7):1688-1694.
Brown et al., "Stable and heritable gene silencing in the malaria vector *Anopheles stephensi*," *Nucleic Acids Research*, Jun. 13, 2003, 31(150:e85.
Chi et al., "Genomewide view of gene silencing by small interfering RNAs," PNAS, May 27, 2003, 100(11):6343-6346.
Chicas et al., "Characteristics of post-transcriptional gene silencing," *EMBO reports*, Sep. 28, 2001, 2(11):992-996.
Chuang et al., "Specific and heritable genetic interference by double-stranded RNA in *Arabidopsis thaliana*," PNAS, Apr. 25, 2000, 97(9):4985-4990.
Cottrell et al., "Silence of the strands: RNA interference in eukaryotic pathogens," *Trends in Microbiology*, Jan. 2003, 11(1):37-43.
Dillin, "The specifics of small interfering RNA specificity," PNAS, May 27, 2003, 100(11):6289-6291.
Feinburg et al., "Transport of dsRNA into Cells by Transmembrane Protein SID-1," *Science*, Sep. 12, 2003, 301:1545-47.
Fire at al., "Potent and specific genetic interference by double-stranded RNA in *Caenorhabditis elegans*," *Nature*, Feb. 19, 1998, 391:806-811.
Firon et al., "Identifying essential genes in fungal pathogens of humans," *Trends in Microbiology*, Oct. 2002, 10(10):456-62.
Hamilton et al., "Two classes short interfering RNA in RNA silencing," *EMBO*, Jul. 16, 2002, 21(17):4671-4679.
Hammond et al., "Post-transcriptional gene silencing by double stranded RNA," *Nature*, Feb. 2001; 2:110-117.
Hannon, "RNA interference," *Nature*, Jul. 11, 2002, 418:244-251.
Heidencreich et al., "AML1/MTG8 oncogene suppression by small interfering RNAs supports myeloid differentiation of t(8;21)-positive leukemic cells," *Blood*, Apr. 15, 2003, 101(8):3157-3163.
Himber et al., "Transitivity-dependent and -independent cell-to-cell movement of RNA silencing," *EMBO*, Jul. 10, 2003, 22(17):4523-4533.
Jorgensen, "RNA traffics information systematically in plants," PNAS, Sep. 3, 2002, 99(18):11561-11563.
Kamath et al., "Effectiveness of specific RNA-mediated interference through ingested double-stranded RNA in *Caenorhabditis elegans*," *Genome Biology*, 2000, 2(1):research0002.1-0002.9.
Klahre et al., "High molecular weight RNAs and small interfering RNAs induce systemic posttranscriptional gene silencing in plants," PNAS, Sep. 3, 2002, 99(18):11981-11986.

(Continued)

*Primary Examiner*—Sean McGarry
*Assistant Examiner*—Louis Wollenberger
(74) *Attorney, Agent, or Firm*—Herbert L. Ley, III; Jay Z. Zhang; Myriad IP Department

(57) ABSTRACT

The present invention provides novel methods for manipulating levels of expression of gene products using RNA interference (RNAi). The methods disclosed can be used to investigate gene function, to create disease-resistant organisms, and to treat disease.

34 Claims, 5 Drawing Sheets

OTHER PUBLICATIONS

Lipardi et al., "RNAi as Random Degradative PCR: siRNA Primers Convert mRNA into dsRNAs that Are Degraded to Generate New siRNAs," *Cell*, Nov. 2, 2001, 107:297-307.

Malhotra et al., "Double-stranded RNA-mediated gene silencing of cysteine proteases (falcipain-1 and -2) of *Plasmodium falciparum*," *Molecular Microbiology*, 2002, 45(5):1245-1254.

Mangeot et al., "A universal transgene silencing method based on RNA interference," *Nucleic Acids Research*, 2004, 32(12):e102 (6 pages).

Martens et al., "RNAi in *Dictyostelium*: The Role of RNA-directed RNA Polymerases and Double-stranded RNase," *Molecular Biology of the Cell*, Feb. 2002, 13:445-453.

Ngo et al., "Double-stranded RNA induces mRNA degradation in *Trypanosoma brucei*," *Proc Natl Acad Sci.*, Dec. 1998, 95:14687-14692.

Nishikura, "A Short Primer on RNAi: RNA-Directed RNA Polymerase Acts as a Key Catalyst," *Cell*, Nov. 16, 2001, 107:415-418.

Pandolfini et al., "Expression of self-complementary hairpin RNA under the control of the rolC promoter confers systemic disease resistance to plum pox virus without preventing local infection," *BMC Biotechnology*, Jun. 25, 2003, 3:1-15.

Roignant et al., "Absence of transitive and systemic pathways allows cell-specific and isoform-specific RNAi in *Drosophila*," *RNA*, 2003, 9(3):299-308.

Schultheiss et al., "A Small GTP-Binding Host Protein Is Required for Entry of Powdery Mildew Fungus into Epidermal Cells of Barley," *Plant Physiology*, Apr. 2002, 128(4):1447-1454.

Schwarz et al., "Evidence that siRNAs Function as Guides, Not Primers, in the *Drosophila* and Human RNAi Pathways," *Molecular Cell*, Sep. 2002, 10:537-548.

Shuey et al., "RNAi: gene-silencing in therapeutic intervention," *Drug Discovery Today*, Oct. 2002, 7(20):1040-1046.

Sijen et al., "On the role of RNA Amplification in dsRNA-Triggered Gene Silencing," *Cell*, Nov. 16, 2001, 107:465-476.

Tang et al., "A biochemical framework for RNA silencing in plants," *Gene & Development*, Nov. 14, 2002, 17:49-63.

Tuschul et al., "Targeted mRNA degradation by double-stranded RNA in vitro," *Genes & Development*, Oct. 28, 1999, 13:3191-3197.

Vaistij et al., "Spreading of RNA Targeting and DNA Methylation in RNA Silencing Requires Transcription of the Target Gene and a Putative RNA-Dependent RNA Polymerase," *The Plant Cell*, Apr. 2002, 14:857-867.

Valdes et al., "Using Double-stranded RNA to Prevent in Vitro and in Vivo Viral Infections by Recombinant *Baculovirus*," *Journal of Biological Chemistry*, May 23, 2003, 278(21):19317-19324.

Van Houdt et al., "RNA Target Sequences Promote Spreading of RNA Silencing," *Plant Physiology*, Jan. 2003, 131:245-253.

Vanitharani et al., "Short interfering RNA-mediated interference of gene expression and viral DNA accumulation in cultured plant cells," *PNAS*, Aug. 5, 2003, 100(16):9632-9636.

Vaucheret et al., "Post-transcriptional gene silencing in plants," *Journal of Cell Science*, 2001, 114:3083-3091.

Wagner et al., "Double-stranded RNA poses puzzle," *Nature*, Feb. 19, 1998, 391:744-745.

Waterhouse et al., "Exploring Plant Genomes by RNA-induced Gene Silencing," *Nature Reviews Genetics*, Jan. 2003; 4:29-37.

Wesley et al., "Construct design for efficient, effective and high-throughput gene silencing in plants," *The Plant Journal*, 2001; 27(6):581-590.

Wilkinson et al., "RNA Interference Identifies Two Hydroperoxide Metabolizing Enzymes That Are Essential to the Bloodstream Form of the African Trypanosome," *The Journal of Biological Chemistry*, Aug. 22, 2003; 278(34):31640-31646.

Winston et al., "Systemic RNAi in C. elegans Requires the Putative Transmembrane Protein SID-1," *Science*, Mar. 29, 2002, 295:2456-2459.

Brummelkamp et al., "A System for Stable Expression of Short Interfering RNAs in Mammalian Cells", *Science*, Apr. 19, 2002, 296:550-553.

Campbell et al., "Knockdown of chimeric glucocerebrosidase by green fluorescent protein-directed small interfering RNA", *Genetics and Molecular Research*, Jun. 14, 2004, 3(2):282-287.

Caplen et al., "Specific inhibition of gene expression by small double-stranded RNAs in invertebrate and vertebrate systems", *Proc. Natl. Acad. Sci. USA*, Aug. 14, 2001, 98(17):9742-9747.

Caplen et al., "Specific inhibition of gene expression by small double-stranded RNAs in invertebrate and vertebrate systems", *Proc. Natl. Acad. Sci. USA*, Aug. 14, 2001, 98(14):9742-9747, Supplementary Material, Table 2. Sequences of RNA oligonucleotides, 1 page.

Castanotto et al., "Functional siRNA expression from transfected PCR products", *RNA Journal*, 2002, 8:1454-1460.

Chiu et al., "RNAi in Human Cells: Basic Structural and Functional Features of Small Interfering RNA", *Molecular Cell*, Sep. 2002, 10:549-561.

Chiu et al., "RNAi in Human Cells: Basic Structural and Functional Features of Small Interfering RNA", *Molecular Cell*, Sep. 2002, 10:549-561. Supplemental Data: Description, Figure S1, Figure S2, 3 pages.

Doench et al., "siRNAs can function as miRNAs", *Gene & Development*, 2003, 17:438-442.

Donze et al., "RNA interference in mammalian cells using siRNAs synthesized with T7 RNA polymerase", *Nucleic Acids Research*, 2002, 30(10⊖46):1-4.

Elbashir et al., "Analysis of gene function in somatic mammalian cells using small interfering RNAs", *Methods*, 2002, 26:199-213.

Elbashir et al., "Duplexes of 21-nucleotide RNAs mediate RNA interference in cultured mammalian cells", *Nature*, May 24, 2001, 411:494-498.

Elbashier et al., "Functional anatomy of siRNAs for mediating efficient RNAi in Drosophila melanogaster embryo lysate", *The EMBO Journal*, Dec. 3, 2001, 20(23):6877-6888.

Holen et al., "Positional effects of short interfering RNAs targeting the human coagulation trigger Tissue Factor" *Nucleic Acids Research*, Apr. 2002, 30(8):1757-1766.

Lee et al., "Expression of small interfering RNAs targeted against HIV-1 rev transcripts in human cells", *Nature Biotechnology*, May 2002, 19:500-505.

Leirdal et al., "Gene silencing in mammalian cells by preformed small RNA duplexes", *Biochemical and Biophysical Research Communications*, 2002, 295:744-748.

Martinez et al., "Single-Stranded Antisense siRNAs Guide Target RNA Cleavage in RNAi", *Cell*, Sep. 6, 2002, 110:563-574.

Miyagishi et al., "U6 promoter-driven siRNAs with four uridine 3' overhangs efficiently suppress targeted gene expression in mammalian cells", *Nature Biotechnology*, May 2002, 20:497-500.

Nagy et al., "Small interfering RNAs suppress the expression of endogenous and GFP-fused epidermal growth factor receptor (erbB1) and induce apoptosis in erbB1-overexpressing cells", *Exp Cell Res.*, Apr. 15, 2003, 285(1):39-49.

Parrish et al., "Functional Anatomy of a dsRNA Trigger: Differential Requirement for the Two Trigger Strands in RNA Interference", *Molecular Cell*, Nov. 2000, 6:1077-1087.

Paddison et al., "Short hairpin RNA's (shRNAs) induce sequence-specific silencing in mammalian cells", *Gene & Development*, Apr. 15, 2002, 16(8):948-958.

Paul et al., "Effective expression of small interfering RNA in human cells", *Nature Biotechnology*, May 2002, 20:505-508.

Rubinson et al., "A lentivirus-based system to functionally silence genes in primary mammalian cells, stem cells and transgenic mice by RNA interference", *Nature Genetics*, Mar. 2003, 33:401-406.

Semizarov et al., "Specificity of short interfering RNA determined through gene expression signatures", *Proc. Natl. Acad. Sci. USA*, May 27, 2003, 100(11):6347-6352.

Sui et al., "A DNA vector-based RNAi technology to suppress gene expression in mammalian cells", *Proc. Natl. Acad. Sci. USA*, Apr. 16, 2002, 99(8):5515-5520.

Tiscornia et al., "A general method for gene knockdown in mice by using lentiviral vectors expressing small interfering RNA", *Proc. Natl. Acad. Sci. USA*, Feb. 18, 2003, 100(4):1844-1848.

Xia et al., "siRNA-mediated gene silencing in vitro and in vivo", *Nature Biotechnology*, Oct. 2002, 20:1006-1010.

Yu et al., "RNA interference by expression of short-interfering RNAs and hairpin RNAs in mammalian cells", *Proc. Natl. Acad. Sci. USA*, Apr. 30, 2002, 99(9):6047-6052.

Yu et al., "RNA interference by expression of short-interfering RNAs and hairpin RNAs in mammalian cells", *Proc. Natl. Acad. Sci. USA*, Apr. 30, 2002, 99(9):6047-6052. Supporting information: Description, Figures 5A-C, 4 pages.

* cited by examiner

Universal Target RNA (UtRNA):

UtRNA in-frame with 3' end of coding region:

UtRNA in-frame with 5' end of coding region:

UtRNA in-frame within coding region:

UtRNA in the 3' untranslated region:

UtRNA in the 5' untranslated region:

Endogenous Expression of Protein (P)

Endogenous and Recombinant Expression of Protein (P)

Introduction of UiRNA targeted to UtRNA

RNAi Induced Silencing of Recombinant Expression

Cell Incapable of Endogenous Expression of Protein (P)

Recombinant Expression of Protein (P)

Introduction of UiRNA targeted to UtRNA

RNAi Induced Silencing of Recombinant Expression

Endogenous and Recombinant Expression of Protein (P)

Introduction of UiRNA targeted to UtRNA

Generation of Secondary siRNAs
During Primary RNAi Response

Transitive RNAi Mediated by Secondary siRNAs
Silences Recombinant and Endogenous Expression

RNA INTERFERENCE USING A UNIVERSAL TARGET

RELATED U.S. APPLICATION

This application claims priority to U.S. Provisional Application Ser. No. 60/416,353, filed on Oct. 4, 2002, the content of which is incorporated herein by reference in its entirety.

FIELD OF THE INVENTION

The present invention generally relates to the field of research into gene product function, and also disease etiology. It describes a method for altering the levels of expression of gene products that can be used in cells, both in culture and in situ.

BACKGROUND OF THE INVENTION

The interference of expression of specific genes following the introduction of double-stranded RNAs (dsRNAs) of corresponding sequence has been observed in a variety of organisms. Initially described as the post-transcriptional gene silencing (PTSG) of transgenes in transgenic plants, similar dsRNA-dependent gene silencing has now been observed in protozoa, fungi, nematodes, insects, and mammals, and the phenomenon is now generally referred to as "RNA interference."

RNA interference (RNAi), which has been defined as the "the process of sequence-specific, post-transcriptional gene silencing in animals and plants, initiated by double-stranded RNA (dsRNA) that is homologous in sequence to the silenced gene" (Elbashir, et al., Nature 411: 494-498 (2001)), has also been described as "the process whereby dsRNA induces the sequence-specific degradation of homologous mRNA" (Chiu & Rana. Molecular Cell 10:549-561 (2002)). Many of the mechanistic details of RNAi first came to light from studies in which long dsRNAs matching the sequences of specific target gene transcripts were introduced into the nematode worm, Caenorhabditis elegans (Fire et al., Nature 391:806-811 (1998)). These early studies inspired many more experiments to be conducted in a variety of organisms, and it is now clear that homologous machinery for RNAi is widely distributed among eukaryotic organisms, including mammals. Although initial attempts to provoke RNAi in mammals and mammalian cells with long dsRNAs failed, it was later determined the failures occurred because such RNA molecules activate an antiviral response that leads to a general inhibition of translation and ultimately cell death. Subsequent studies in a variety of non-mammalian species demonstrated that long dsRNAs introduced into cells are enzymatically cleaved into shorter duplexes comprising two complementary single-stranded RNAs of 21-25 nucleotides (see Sharp, Genes & Dev. 15:485-490 (2001), and references therein). More recent studies have demonstrated that, while dsRNAs of 30 base-pairs or more elicit the aforementioned antiviral response, RNA duplexes comprising two complementary single-strands of 21 nucleotides each, which pair to form a 19 base-pair duplexed region with two nucleotide 3' overhangs (so called small or short interfering RNAs (siRNAs)), can mediate RNAi in cultured mammalian cells without evoking an antiviral response (Elbashir et al., Nature 411:494-498 (2001)). Additionally, when appropriately targeted via their nucleotide sequence, these siRNAs can specifically suppress the expression of both endogenous genes and heterologous transgenes, of corresponding sequence. Even more recent studies have demonstrated that while double-stranded siR-NAs are very effective at mediating RNAi in a variety of cell types, short, single-stranded, hairpin-shaped RNAs can also mediate RNAi, presumably because they are processed into siRNAs by cellular enzymes (Sui et al., Proc. Natl. Acad. Sci. U.S.A. 99:5515-5520 (2002); Yu et al., Proc. Natl. Acad. Sci. U.S.A. 99:6047-6052 (2002); and Paul et al., Nature Biotech. 20:505-508 (2002)). This discovery has significant and far-reaching implications since the production of such small hairpin RNAs (shRNAs) can be readily achieved in vivo by transfecting cells with transcription vectors bearing short inverted repeats separated by a small number of (e.g., six) nucleotides. Additionally, if features are included to ensure the stability of the transcription plasmid, or direct the integration of the transcription cassette into the host cell genome, the RNAi induced by the encoded shRNAs, can be made stable and heritable.

Since it was first exploited to silence specific genes in C. elegans, RNAi has become an irreplaceable tool for molecular, cellular and developmental biologists seeking to discover the functions of specific genes. Although few of the molecular mechanisms of RNAi are known in detail, it is clear that the degradative process involves the assembly of a multisubunit ribonucleoprotein nuclease complex, known as RISC (for RNA-induced silencing complex), which is somehow guided by the antisense strand of an siRNA to a complementary target sequence in a mature RNA transcript, where it catalyzes the cleavage of the targeted transcript. It is also clear that all that is necessary to target a transcript for degradation is that the sequence of the antisense strand of an siRNA be complementary to that of a "target sequence" in the transcript to be degraded. Empirical studies have shown, however, that not all target sequences are equivalent. That is, siRNAs corresponding to different target sequences within the same transcript can exhibit significantly different efficiencies in directing the degradation of the same transcript. Furthermore, at present it is impossible to predict which target sequences will prove to be most effective targets. Practically, if one wants to efficiently silence a particular gene by RNA interference, one must empirically determine which sequences make the best targets by designing and testing siRNAs corresponding to different target sequences. This process is both cumbersome and time consuming.

In all taxa exhibiting RNAi, siRNAs corresponding to a specific target sequence in a gene or transgene (primary siR-NAs or trigger siRNAs), evoke a "primary" RNAi response, wherein the targeted transcript is cleaved in the region of nucleotide sequence complementary to the antisense strand of the siRNA. However, in C. elegans and plants, a "secondary" RNAi response is observed, wherein "secondary" siR-NAs are produced that direct cleavage of the target transcript in regions outside of the original target sequence. In C. elegans, these secondary cleavages occur at sites exclusively 5' of the primary siRNA target sequence, but in plants, these secondary cleavages occur at sites either 5' or 3' of the primary siRNA target sequence. Additionally, if the regions of nucleotide sequence in which secondary RNAi cleavages occur are homologous to other transcripts within the cell, the secondary RNAi response can lead to silencing of transcripts containing highly similar nucleotide sequences, that were not initially targeted by the trigger siRNA. The observed secondary RNAi response has been termed "transitive RNAi," because the sites of cleavage during the secondary response transit along the originally targeted transcript away from the primary target to adjacent regions, or the silencing transits to transcripts that were not initially targeted during the primary RNAi response.

Although the specific mechanisms operating behind the phenomenon of transitive RNAi remain to be elucidated, the taxa that exhibit transitive RNAi also appear to be able to "amplify" the gene silencing response induced by primary siRNAs. Additionally, it has been shown that in *Arabadopsis* and *C. elegans*, transitive RNAi requires the action of putative RNA-dependent RNA polymerases (RdRPs) (Dalmay et al., *Cell* 101:543-553 (2000) and Sijen et al., *Cell* 107:465-476 (2001)). Consequently, it has been hypothesized that in *C. elegans*, transitive RNAi involves an amplification step catalyzed by RdRP, whereby the antisense strand of siRNAs serve as primers for synthesis of dsRNAs by RdRP, using the targeted transcript as the template, and the nascent dsRNAs are subsequently cleaved by an endonuclease (Dicer) to produce secondary siRNAs (Sijen et al., *Cell* 107:465-476 (2001). If the nascent dsRNA so synthesized contains nucleotide sequences highly similar to nucleotides sequences in RNA transcripts not targeted by the initial siRNA during a primary RNAi response, the dsRNA corresponding to these nucleotide sequences will be cleaved to form the "secondary" siRNAs necessary to target these alternate transcripts and transit the silencing to the gene products encoded by these alternate transcripts. This hypothesis is consistent with the observation that, in some studies, siRNAs designed to target a particular member of a gene family, ultimately induced silencing of the entire family of genes.

Although RNAi has proven to be a remarkably powerful tool for investigating gene function in a variety of taxa, as mentioned above, Tuschl and colleagues only recently discovered that 21-nucleotide siRNAs could be used for studying gene function in mammalian cells without evoking a general antiviral response (Elbashir et al., *Nature* 411:494-498 (2001)). Unfortunately, once a gene is selected for siRNA-induced silencing, the choice of which sequences to target by siRNAs is somewhat unclear. Towards this end, Holen and colleagues investigated the efficacy of siRNAs targeted to different positions in the transcript of human coagulation trigger Tissue Factor (hTF) in a variety of human cell types in culture (See Holen et al., *Nucleic Acids Res.* 30:1757-1766 (2002)). In this study several siRNAs corresponding to several target sequences located in hTF transcripts were synthesized and tested for their ability to induce silencing of the hTF gene. Of the several siRNAs synthesized and tested only a few resulted in a significant reduction in expression of hTF, suggesting that accessible siRNA target sites may be rare in some human mRNAs. Further, siRNAs targeting different sites in the hTF mRNA demonstrated striking differences in their ability to silence the expression of hTF. Although, strong positional effects were seen with the siRNAs tested, and regions of high GC content seem to be targeted less efficiently than those of low GC content, Holen and coworkers concluded that the factors determining the differences in siRNA efficiency remain unclear, and that susceptible RNAi target sites in some human genes may be rare.

From a practical perspective, the results of Holen and colleagues suggest that it is difficult, if not impossible to predict, a priori, what sequences to target in a gene to target with siRNAs to induce efficient silencing by RNAi. In addition, there is a growing body of evidence that specific siRNAs selected to silence particular genes may produce unwanted and unanticipated "off-target" effects—altering the expression of untargeted RNA transcripts. Jackson and colleagues recently published the results of a study of off-target gene regulation conducted using a gene expression profiling technique to characterize the specificity of gene silencing by siRNAs in cultured human cells. Their results provide clear evidence that treatment of cells with siRNAs corresponding to different sequences within the same RNA transcript may result in different, but reproducible, off-target silencing effects, at least some of which may be due to partial sequence homology between the affected transcripts and either the sense or the antisense strand of the siRNA employed. They conclude that it may be difficult to select an siRNA sequence that will be absolutely specific for the target of interest (Jackson et al., *Nature Biotech.* 21:635-637 (2003)).

Recent advances in genomics, especially with the completion of the human genome sequence, have lead to the discovery of numerous novel genes of unknown function. Unfortunately, advances in our ability to sequence genomes, and identify novel genes within them have far outstripped our ability to determine the function of the gene products of these novel genes. Classically, gene function has been addressed in vivo by two distinct approaches: overexpression of the gene product and underexpression of the gene product.

High-throughput methodology in biotechnology is largely responsible for the recent explosive growth of knowledge in genomics and proteomics—two specialty fields that are relatively new to the larger field of molecular biology. In the realm of pharmaceutical research and development, high-throughput technologies, genomics and proteomics, have had a profound impact on therapeutic drug development (Kennedy. EXS. 89:1-10 (2000)). Such technologies have issued in a "new millennium" of drug discovery (Cunningham. J. Pharmacol. Toxicol. Methods. 44:291-300 (2000)), and have provided a catalyst for change in drug discovery paradigms (Hanke. J. Law Med. Ethics. 28(4 Suppl): 15-22 (2000)). Such technologies have the potential for greatly increasing the speed of drug development, and for reducing the associated costs—both of these factors being critically important given the current economic and social climate. Clearly, significant improvements in the ability of research scientists to (a) selectively overexpress specific target genes, (b) selectively block the expression of specific target genes, (c) screen large numbers of target genes for their cellular functions, and (d) ultimately determine how overexpression or underexpression of specific target genes affect desired outcomes in mammalian cells, will be of benefit to society.

Traditionally, RNAi has been applied to investigate the function of genes in a one-target-at-a-time mode. This approach has proven very useful in analyzing the function of a limited number of genes in the model organisms *C. elegans* and *D. melanogaster*. The use of microarray-based RNAi technology using siRNAs should greatly facilitate the investigation of functions for hundreds or thousands of mammalian genes simultaneously in a parallel fashion. However, given the findings of Holen et al. and Jackson et al., discussed above, the choice of what specific sequence within an mRNA to target with siRNAs of corresponding sequence is completely unclear. Further, although microarray-based RNAi technology will perhaps allow the empirical identification of sequences that will serve as ideal targets of RNAi, the process of synthesizing and testing numerous siRNAs is laborious and costly.

While RNAi holds much promise for high-throughput analyses designed to determine gene function through the silencing of large numbers of genes, the method is not without complications and challenges. Perhaps the most fundamental challenge is how to pick a target sequence within the target transcript that will allow for the efficient silencing of the target gene, along with minimal unintended and undesired off-target effects. Despite numerous studies in which siRNAs have been employed to induce gene silencing, no definitive rules have evolved to assist researchers in picking the most effective sequences to target within a given transcript. Although there are general guidelines to help researchers narrow their choices for target sequences, researchers must still use a trial and error approach to empirically determine what individual siRNAs work best, and what siRNAs have minimal off-target effects. Given these limitations and the many potential and varied applications of RNAi, there is a clear need for alternative approaches and techniques for altering gene expression by siRNAs, especially with regards to high-throughput applications.

SUMMARY OF THE INVENTION

The present invention provides novel methods for altering levels of expression of a plurality of gene products using RNA interference (RNAi) induced by a "Universal interfering RNA" (UiRNA) directed towards a commonly-shared "Universal target RNA" (UtRNA). The UtRNA, which is incorporated into a plurality of chimeric RNA transcripts, each comprising a different subject RNA, whose cellular concentration is to be decreased, may be located at several locations within the chimeric transcripts, depending upon the application. In addition, when the subject RNAs encode polypeptides, a UtRNA encoding a readily detectable peptide (e.g., epitope tag, fluorescent peptide, enzymatic tag, etc.) can be chosen and cloned in-frame with the subject RNAs such that fusion proteins are produced by translation of the chimeric RNA transcripts. Advantageously, such a UtRNA-encoded peptide tag can be used to readily quantitate the level of expression of the fusion proteins under study. The methods of the present invention can be readily employed to investigate the function of any number of gene products, and the more gene products being investigated, the greater the benefits of the methods. Preferably the method is employed to selectively manipulate the expression levels of a plurality of distinct gene products in cultured target cells, in a parallel, high-throughput, format.

Importantly, the expression of all gene products encoded by chimeric RNA transcripts bearing a common UtRNA can be manipulated through RNAi induced by the same UiRNA, which is specifically designed to target the UtRNA. As such, the UiRNA can be a double-stranded siRNA, or a single-stranded shRNA. Furthermore, the UiRNA can be introduced into the target cells by any of the various means known in the art. In one set of embodiments, introduction of the UiRNA is by way of a DNA that directs the in vivo transcription of an RNA, or RNAs within the target cells or organisms. In certain embodiments the in vivo transcribed RNA can be a small hairpin RNA (shRNA) that is processed by cellular ribonucleases (RNases) to produce an siRNA-like UiRNA. In other embodiments, two complementary siRNAs can be transcribed in-vivo, and annealing of the two individual strands results in the formation of a double-stranded siRNA-like UiRNA. In some of these embodiments the DNA that directs the in-vivo expression of the UiRNA is introduced into the target cells or organisms before the introduction of expression vectors directing the expression of the chimeric RNA transcripts. In certain of these embodiments, an expression cassette—and preferably an inducible expression cassette—is stably introduced into the target cells or organisms to produce transgenic target cells or organisms that can express UiRNA when required to do so. In another set of embodiments, the UiRNA is synthesized in vitro and subsequently introduced to the target cells. Such in vitro synthesized UiRNA may be chemically or enzymatically synthesized and may be the double-stranded UiRNA itself, or may be an shRNA that is processed by RNases, in vivo or in vitro, to produce the UiRNA.

The UtRNA can be composed of any sequence of nucleotides that facilitates the efficient RNAi of all chimeric RNA transcripts in which it appears, regardless of where it occurs within the transcript, and regardless of what target RNA is included in the same transcript. In one set of embodiments, the UtRNA is placed in a non-coding region of the chimeric RNA transcript—either the 5' untranslated region (UTR), or the 3' UTR. In another set of embodiments, the UtRNA encodes a peptide and is inserted in-frame with the coding region of the target RNA—either in-frame with either end of the coding region, or within the coding region itself—thereby creating a chimeric open reading frame that is translated into a fusion protein. In this set of embodiments, the UtRNA preferably encodes a peptide, which can be used to detect and quantitate the level of expression of the fusion protein.

Advantageously, the methods of the present invention provide a means for targeting a plurality of recombinantly expressed gene products for RNA interference, by providing a plurality of expression vectors that direct the expression of a plurality of chimeric RNA transcripts, each comprising a different, unique subject RNA preferably encoding a particular gene product, and a common UtRNA. These expression vectors are then introduced into target cells or organisms, which are capable of transcribing the chimeric RNA transcripts and translating the encoded gene products, thereby creating a plurality of transfected target cells or organisms, each collection of target cells or organism transfected with the same expression vector expressing the same chimeric RNA transcript and encoded gene product. In a preferred embodiment the transfected target cells or organisms are arranged in an addressable array, with cells or organisms transfected with a single expression vector exclusively occupying a specific address within the array. A UiRNA that is capable of inducing RNAi by targeting the common UtRNA shared by all expression vectors and chimeric RNA transcripts, in all transfected target cells or organisms can then be introduced into these transfected target cells or organisms to simultaneously reduce expression of all recombinantly expressed gene products. As mentioned above, the means by which the UiRNA is introduced into the transfected target cells include introduction by way of a DNA that directs the in vivo transcription of RNA, as well as by introduction of in vitro synthesized RNA. Also, as mentioned above, the RNA transcribed or synthesized can be a double-stranded siRNA-like UiRNA, or can be a shRNA that is processed by cellular RNases to form the UiRNA.

The methods of the present invention also provide a means of investigating the effects of altered levels of gene product expression for a plurality of gene products by providing a plurality of expression vectors that are introduced into a cell and direct the expression of a chimeric RNA transcripts, each encoding a particular gene product and bearing a common UtRNA. These expression cassettes are introduced into target cells that are capable of transcribing and translating the chimeric RNA transcripts; thereby creating a plurality of transfected target cells that overexpress the gene product cloned into the expression cassette (also referred to as the gene product under study). At some point in time relative to the introduction of the expression cassette, UiRNA is introduced into the transfected target cells. The introduced UiRNA, which corresponds in sequence to the UtRNA, induces RNAi and promotes the degradation of the chimeric RNA transcripts bearing the UtRNA. The net result is a reduction in the expression of the particular gene product expressed from the chimeric RNA transcript produced in that cell. Differences in the transfected target cells before and after introduction of the UiRNA are detected and measured, and are preferably correlated with differences in the levels of expression of the gene product. Using such an approach the effects of altered gene expression are observed, and the function of the gene product whose expression levels are manipulated is revealed.

Importantly, the methods of the present invention can be employed to manipulate levels of expression of gene products in cells, tissues, or organisms transfected with the expression cassettes of the present invention. In particular, the type of RNA introduced to induce RNAi, the amount of RNA introduced (dosage), the means by which it its introduced (route and method of introduction—e.g., lipofection, electroporation or synthesis in vivo) can be adjusted to produce the quantitative and temporal manipulation of gene product expression desired.

The methods of the present invention can be used with any type of cell that (1) can be transfected with the expression cassettes of the present invention, (2) will direct the production of the chimeric RNA transcripts of the present invention, (3) to which UiRNA can be introduced, and (4) that exhibits RNAi. Importantly, the methods of the present invention can be used in a variety of cell types or cell lines, and different cell types or cell lines can be chosen to create different experimental scenarios. In particular, cell lines that show distinctly different endogenous levels of expression of the gene product under study, or no expression of the gene product under study, can be chosen to augment the methods of the present invention for studying gene product function. Additionally, the methods of the present invention can be employed in cell types, cell lines, tissues or organisms that exhibit transitive RNAi, with very different effect. These different scenarios are presented in more detail below.

The present invention further provides kits that can be used to either target a plurality of recombinantly expressed gene products for RNA interference, or to determine the effects of altered levels of gene product expression. These kits can comprise one or more vectors, including expression vectors having an expression cassette comprising a multiple cloning site and a UtRNA, wherein the expression cassette is capable of directing the expression of a recombinant transcript comprising the UtRNA and any nucleotide sequence inserted into the multiple cloning site (a subject RNA). The kits further comprise either interfering RNAs that effectively induce the RNAi of expression of the recombinantly expressed gene product, or transcription vectors that direct the in vivo transcription of such RNAs. These RNAs, which are designed to induce RNAi by specifically targeting the UtRNA contained in the recombinant transcripts, correspond in sequence to the UtRNA.

In one set of embodiments, the present invention provides arrays of cultured cells, tissues, or organisms wherein the cells, tissues, or organisms at specific addresses in the array have been transfected with expression vectors comprising a chimeric expression cassette having a nucleotide sequence encoding a particular gene product, and a common UtRNA. The chimeric expression cassettes in these transfected and arrayed cultures of cells, tissues or organisms are capable of directing the expression of chimeric RNA transcripts encoding different gene products, but bearing the same UtRNA. Consequently, the expression of all gene products in all transfected and arrayed cultures of cells or organisms can be subjected to a reduction of expression by inducing RNAi with a common UiRNA, that is administered to the cells or organisms. Such arrays of transfected cultured cells should be made up of at least 2, 3, 4, 5, preferably 6, 8 or 12, and more preferably 16, 24, 32, 36, 40, 48, 56, 60, 64, 72, 80, 84, 88, 96 or more groups of cells or organisms transfected with different chimeric expression vectors, all capable of directing the expression of chimeric RNA transcripts encoding different gene products, but bearing a common UtRNA. Such arrays of transfected cultured cells, tissues, or organisms can be arranged in strips of 2, 3, 4, 6, 8, 12, or more culture tubes or vessels, or in 96-well plates, or the likes. Cells in such arrays can be grown in suspension, or as a monolayer on a substrate. Alternatively, microarrays of transfected cells can be made in a monolayer of cells attached to a common substrate as described by Sabatini in U.S. Pat. No. 6,544,790, which is incorporated by reference herein in its entirety.

In another set of embodiments, the present invention further provides methods by which the involvement and/or role of a plurality of gene products in pathogenesis, genetic disorders, or infectious diseases can be assessed. For these embodiments, the nucleotide sequences encoding gene products suspected or known to be associated with or involved in a particular infectious disease or genetic disorder are inserted into the expression cassettes of the present invention. These expression cassettes, which may be further incorporated into expression vectors, are introduced into cells of an appropriate cell type or line to produce transfected target cells or tissue, or into whole organisms to produce transfected organisms. Once inside the cells or organisms, the expression cassettes direct the production of chimeric RNA transcripts that encode the different suspect gene products, but bear a common UtRNA. The levels of expression of the encoded gene products can be further manipulated in the transfected target cells or organisms by the introduction of RNA(s) corresponding in sequence to the UtRNA that induce RNAi by targeting the UtRNA (UiRNAs). The transfected target cells or organisms can then be examined in the presence and absence of such UiRNAs, to determine whether the gene product whose expression level is being manipulated by RNAi, does indeed play a role in pathogenesis, genetic disorders, or infectious diseases. For example, the transfected target cells or organisms can be exposed to an infectious agent in the absence of UiRNA (conditions under which expression of the gene product encoded in the chimeric RNA transcripts will be enhanced), or in the presence of UiRNA (conditions under which expression of the gene product encoded in the chimeric RNA transcripts will be silenced or reduced). If the gene product under study plays a role in the infectious cycle of the infectious agent, differences in the health of the transfected target cells or organisms will likely be observed between identical cultures of the transfected target cells or organisms maintained under the two different treatment regimes (i.e., in the presence or absence of UiRNA).

In still another set of embodiments, the present invention also provides methods of treating disease by manipulating the levels of expression of a particular gene product. Such methods may be applied to human cells, tissues or patients, or may be applied to non-human cells, tissues or organisms. For humans, the method comprises the steps of administering to a person in need of such treatment a chimeric expression cassette comprising a nucleotide sequence that directs the expression of a chimeric RNA transcript encoding a particular gene product and a UtRNA, and introducing into the person an RNA that induces RNAi of expression of the encoded gene product by targeting the UtRNA in the recombinant transcript. As above, the step of introducing the siRNA can be by way of introducing a DNA that directs the in vivo transcription of an RNA that induces RNAi, or alternatively, can be by way of introducing an RNA that has been synthesized in vitro and induces RNAi in vivo. The RNA introduced can be a double-stranded siRNA, or a single-stranded hairpin RNA that is processed into an siRNA by RNases. RNAs that are synthesized in vitro can be synthesized either enzymatically or chemically. The RNA can include modified nucleotides of any type, as well as other chemical modifications that impart characteristics such as improved stability, resistance to nucleases, greater efficacy, etc.

The diseases being treated in human can be genetic disorders or infectious diseases. The infectious diseases can be diseases caused by any type of pathogen, including viruses, bacteria, fungi, parasitic protozoa, nematodes, etc. Viral diseases that can be treated include diseases caused by human immunodeficiency virus (HIV), hepatitis B virus (HBV), hepatitis C virus (HCV), human herpesvirus 1 (HSV1), human herpesvirus 2 (HSV2), human influenza A (HIA), and the like. Also, the gene products whose expression levels are being manipulated can be mammalian gene products, human gene products or pathogen gene products, including viral gene products.

Advantageously, in cells or organisms that naturally exhibit, or are made to exhibit, transitive RNAi, the methods of the present invention further provide a means to reduce the expression of recombinantly expressed gene products, as well as endogenous gene products. In such organisms, or the cells from such organisms, RNAi induced gene silencing caused by UiRNAs that target UtRNAs in expressed chimeric RNA transcripts would likely transit or propagate to transcripts bearing sequences either identical to, or highly similar to the sequence encoded in the chimeric transcripts. Hence, in such cells or organisms the methods of the present invention can be used to promote the silencing of expression of any endogenous gene product without having to design or administer gene-specific siRNAs. Further, multiple endogenous gene products can potentially be silenced in such organisms or cells using a single UiRNA that is targeted to the UtRNA in a plurality of chimeric RNA transcripts that also bear the sequences encoding the endogenous gene products to be silenced (subject RNAs).

DETAILED DESCRIPTION OF THE INVENTION

1. Definitions

Figure 1:
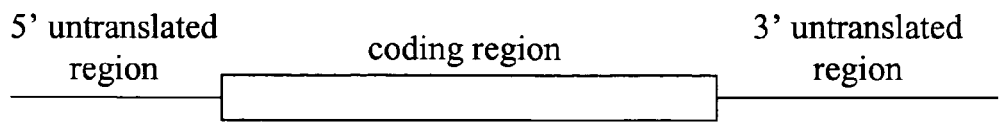
FIG. 1 depicts five different exemplary configurations of chimeric RNA transcripts that can be produced from five different types of expression cassettes of the present invention. Each of the five configurations includes a 5' UTR, 3' UTR, nucleotide sequence that encodes the gene product whose expression is to be manipulated (the subject RNA), and a universal target RNA (UtRNA). In the first two examples the UtRNA is found in non-coding sequence, and the last three examples the UtRNA encodes a peptide, preferably a readily detectable peptide, and is cloned in-frame with the open reading frame encoding a particular gene product.
Figure 1:
Figure 1:
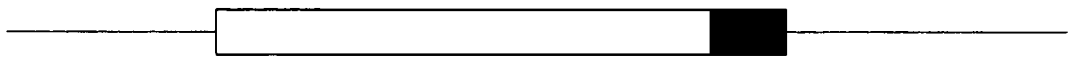
Figure 1:
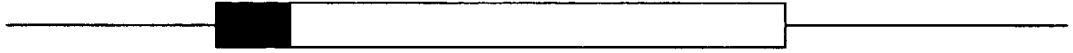
Figure 1:
Figure 1:
Figure 1:

As used herein, the term "RNA interference," or "RNAi," refers to the process whereby sequence-specific, post-transcriptional gene silencing is initiated by an RNA that is homologous in sequence to the silenced gene. RNAi, which occurs in a wide variety of living organism and their cells, from plants to humans, has also been referred to as post-transcriptional gene silencing (PTGS) and co-suppression in different biological systems. The sequence-specific degradation of mRNA observed in RNAi, is mediated by small (or short) interfering RNAs (siRNAs).

As used herein, the term "transitive RNA interference," refers to the process whereby RNAi induced by an administered or introduced siRNA (the primary siRNA) leads to the in vivo formation of a population of secondary siRNAs, generally corresponding to nucleotide sequences nearby, but distinct from, the nucleotide sequence targeted by the primary siRNA. These secondary siRNAs induce a secondary RNAi response in which transcripts bearing nucleotide sequences corresponding to the secondary siRNAs are targeted for endonucleolytic cleavage. The term "transitive RNAi" refers to the ability of secondary siRNAs to "transit" the RNAi gene-silencing phenomenon from the originally targeted transcript to different transcripts bearing regions of nucleotide sequence homologous to the sequences of the secondary siRNAs.

As used herein, the term "interfering RNA" means an RNA molecule capable of directing the degradation of an RNA transcript having a nucleotide sequence at least a portion of which is substantially the same as that of the interfering RNA, through the mechanism of RNA interference (RNAi). As known in the art, interfering RNAs can be "small interfering RNAs," or siRNAs, composed of two complementary single-stranded RNAs that form an intermolecular duplex. Interfering RNAs can also be "short hairpin RNAs," or shRNAs, composed of a single-stranded RNA with two self-complementary regions that allow the RNA to fold back upon itself and form a stem-loop structure with an intramolecular duplex region and an unpaired loop region. Finally, in some circumstances (See Martinez et al., *Cell* 110:563-574 (2002)), interfering RNAs can be single-stranded antisense RNAs of 19 to 29 nucleotides that are complementary to a target sequence.

The terms "small interfering RNA" (also sometimes referred to as short interfering RNA) or "siRNA," as used herein, refer to the mediators of RNAi—RNA molecules capable of directing sequence-specific, post-transcriptional gene silencing of specific genes with which they share nucleotide sequence identity or similarity. Recent experiments have shown that the siRNAs that are most effective in mammalian cells are duplexes composed or two complementary 21 nucleotide single-stranded RNAs that anneal to form a duplexed region of 19 basepairs and single-stranded overhangs of 2 nucleotides at their 3' ends. In some organisms (e.g., *C. elegans, D. melanogaster* and various plants) these siRNAs can be created by the nucleolytic processing of longer dsRNAs. In mammalian cells they apparently can also be produced from short (i.e., less than 30 basepairs) hairpin RNAs, or shRNAs.

The term "small hairpin siRNA," "short hairpin siRNA," or "shRNAs," as used herein, refers to siRNAs composed of a single strand of RNA that possesses regions of self-complementarity that cause the single strand to fold back upon itself and form a hairpin-like structure with an intramolecular duplexed region containing at least 19 basepairs. Importantly, because they are single-stranded, shRNAs can be readily expressed from single expression cassettes.

The term "knock down," as used herein, describes the condition created by RNAi, wherein the expression of a particular gene-product, or the cellular concentration of a particular RNA transcript, is reduced or eliminated by the sequence-specific, post-transcriptional gene silencing initiated by siRNAs that are homologous in sequence to the gene encoding said gene product.

The term "subject RNA," as used herein, refers to an RNA whose cellular concentration is to be altered, manipulated or reduced, or knocked down, by the action of an interfering RNA targeting the universal target RNA, but not the subject RNA.

As used herein, the term "chimeric RNA transcript" means an RNA transcript comprising a subject RNA operably linked to a universal target RNA to create a single RNA that does not naturally occur in nature.

The term "operably linked," when used in the context of a chimeric RNA transcript, means joined directly or indirectly such that the universal target RNA facilitates the reduction in concentration of at least the subject RNA when the chimeric RNA transcript is subjected to RNA interference induced by a universal interfering RNA.

The term "universal target RNA," or UtRNA, as used herein, refers to a common RNA that is incorporated into a plurality of chimeric RNA transcripts, and serves to impart upon the chimeric RNA transcripts a susceptibility to degradation by RNA interference promoted by a "universal interfering RNA" targeting the universal target RNA.

The term "in vitro transcription," as used herein, describes the process whereby a new (nascent) RNA molecule is synthesized, outside of a living cell, from individual ribonucleotides-triphosphates by an enzyme (usually RNA polymerase), using a DNA molecule as a template to specify the sequence of the nascent RNA.

As used herein, the term "transcription vector" refers to a vector containing, at least, a promoter that directs transcription by an RNA polymerase, a transcription template sequence, and a transcription terminator sequence, such that an RNA transcript can be synthesized from the transcription vector.

2. Overview and Embodiments

The present invention describes a novel method for manipulating the expression of a plurality of gene products within a cell or organism using a UiRNA that is designed to specifically target a UtRNA. The methods of the present invention, which can be employed in numerous alternative embodiments, can be used for a variety of purposes. Specifically, the methods of the present invention can be used to target a plurality of recombinantly expressed gene products for RNAi using a single, common UiRNA. The methods of the present invention can also be used to determine the effects of altered levels of gene expression, preferably for a plurality of genes, and preferably in arrayed collections of cells. The methods of the present invention can also be used to identify gene products that play important roles in pathogenesis, genetic disorders, and infectious diseases.

The present invention also provides kits that can be used to target a plurality of recombinantly expressed gene products for RNA interference using a single, common UiRNA. The present invention further provides for arrays of transfected cells, preferably created through the use of transfection microarrays, in which a single UiRNA can be used to induce RNAi of a plurality of gene products, each expressed in a collection of cells at a specific address within the array. The methods of the present invention, when utilized in organisms or cells exhibiting transitive RNAi, provide a method of reducing the expression of a plurality of endogenous genes, using a UiRNA that is targeted to a UtRNA, when a nucleotide sequence encoding the endogenous gene, or a homologue thereof, is included along with a UtRNA in a single chimeric RNA transcript. Consequently, in organisms or cells that either naturally exhibit transitive RNAi, or are made to carry out transitive RNAi, the methods of the present invention provide a method for treating disease that involves reducing the cellular concentration of gene products encoded by endogenous RNA transcripts by first targeting a chimeric RNA transcript bearing a UtRNA and encoding a gene product whose endogenous expression is desired to be reduced, using UiRNA-induced RNAi to initially reduce the expression of the recombinantly expressed gene product, and allowing secondary siRNAs generated during that process to transit and cause the RNAi-mediated degradation of endogenous transcripts encoding the target gene product, and homologues thereof. These various embodiments are described in detail below.

It should be stressed that the methods of the present invention can be expected to have very different effects, and hence different uses, in cells and organisms that naturally exhibit transitive RNAi, or can be made to do so, as opposed to those that do not. In the former—cells and organisms that naturally exhibit transitive RNAi, or can be made to do so—the methods of the present invention can be expected to result in a net reduction of expression of the plurality of gene products encoded in the plurality of expression vectors tested. This net reduction of expression results from the production of secondary siRNAs, which can transit to target homologous endogenous transcripts and promote their endonucleolytic cleavage. In such cells and organisms, the methods of the present invention can be expected to reduce the expression of the gene products under study to levels below those naturally occurring in untreated target cells. In contrast, in cells or organisms that do not exhibit transitive RNAi, the methods of the present invention can be expected to result in levels of expression of the plurality of gene products encoded in the plurality of expression vectors tested somewhere between those of untransfected target cells (i.e., the natural background levels), and cells transfected with the expression vectors of the present invention (i.e., the overexpressed levels). In these cells and organisms, the methods of the present invention can be used to investigate the effects of overexpression of the plurality of gene products encoded in the plurality of expression vectors tested, followed by a partial reduction in their expression level. In such cells and organisms the methods of the present invention can be useful for investigating the disregulation of expression of the plurality of gene products encoded in the plurality of expression vectors tested.

The present invention provides a method for manipulating the levels of expression of a plurality of gene products using a UiRNA that is targeted to a UtRNA incorporated into chimeric RNA transcripts expressed from expression cassettes or expression vectors in target cells. These chimeric RNA transcripts, which can encode any gene product, comprise a subject RNA and a UtRNA, and the UtRNA can be incorporated into the chimeric RNA transcripts in any location with respect to the subject RNA (FIG. 1). The method overcomes the limitations faced in the prior art. First, the same UtRNA is incorporated into a plurality of chimeric RNA transcripts, a single type of UiRNA, which targets that that UtRNA, can be used to reduce the expression of all gene products encoded by that plurality of chimeric RNA transcripts. Second, the UtRNA targeted by the UiRNA, and the UiRNA employed, can be selected and tested in advance, in order to assure that (a) UiRNA-mediated, RNAi-induced, gene silencing works effectively and without regard to the location of the UtRNA in the chimeric RNA transcripts, or the identity of the gene product coding sequence included within the chimeric RNA transcripts, and (b) the UiRNA employed results in minimal, or negligible off-target gene silencing. These advantages are discussed in further detail below.

Currently, in order for researchers to use RNAi to effectively silence the expression of specific heterologous recombinant or endogenous gene products, they must design and test specific siRNAs that target that the transcript encoding the particular gene product whose levels of expression they wish to reduce. Each gene to be silenced requires that a specific siRNA, or set of siRNAs, be designed to promote RNAi-induced silencing, and each siRNA designed must be tested for its efficacy. Since not all sequences within transcripts encoding particular gene products are efficiently targeted by corresponding siRNAs, researchers must generally conduct preliminary experiments to empirically determine which sequences, and their corresponding siRNAs, work best for RNAi-mediated gene silencing (see Holen et al., *Nucleic Acids Res.* 30:1757-1766 (2002)).

Similarly, as described above, there is a growing body of evidence that specific siRNAs selected to silence particular genes may produce unwanted and unanticipated "off-target" effects—altering the expression of untargeted RNA transcripts. In fact, treatment of cells with siRNAs corresponding to different sequences within the same targeted RNA transcript has been shown by expression profiling to result in different, but reproducible, off-target silencing effects. Apparently, at least some of these off-target effects may be due to partial sequence homology between the affected transcripts and either the sense or the antisense strand of the siRNA employed, but some could not be explained by sequence homology, leading the researchers to conclude that it may be difficult to select an siRNA sequence that will be absolutely specific for the target of interest (Jackson et al., *Nature Biotech.* 21:635-637 (2003)). Since the UtRNA of the present invention, and the UiRNA which targets it, can be selected and tested in advance, such undesirable off-target effects can be minimized. Furthermore, since the chimeric RNA transcripts of the present invention that encode different gene products in the subject RNA bear the same UtRNA, they can all be silenced by introduction of the same UiRNA. And since Jackson and colleagues have shown that the off-target silencing effects of specific siRNAs are distinct and reproducible, use of the same UiRNA for the induction of RNAi in different target cells bearing different chimeric RNA transcripts, at least results in equivalent off-target silencing effects in all target cells, thereby eliminating any variability that might otherwise result from the introduction of different, transcript-specific, siRNAs to different target cells.

Certainly, incorporating a common UtRNA in a plurality of chimeric RNA transcripts, and targeting those chimeric RNA transcripts for RNAi-induced degradation through the introduction of a single corresponding UiRNA, eliminates the need for designing and testing different gene-specific siRNAs and may reduce or eliminate the variability of silencing effects caused by introduction of different gene-specific siRNAs. Further, a UtRNA and its corresponding UiRNA can be chosen and tested in advance to ensure that (a) the expression of gene products encoded by recombinant transcripts bearing a UtRNA are effectively silenced by introduction of a corresponding UiRNA, and (b) the silencing observed is specific.

Additionally, and advantageously, a UtRNA that functions effectively and specifically in one chimeric RNA transcript, should function equally well in other chimeric RNA transcripts encoding different gene products. Similarly, since UtRNAs can be identified that have little or no similarity to any endogenous nucleotide sequences, UiRNAs targeting these UtRNAs can be expected to have little or no homology-related effect on endogenous gene expression—unless the cell or organism in which the UtRNA/UiRNA system is employed exhibits transitive RNAi. In which case, UiRNA-induced silencing of expression of a chimeric transcript having a subject RNA operably linked to a UtRNA may be expected to "transit" to endogenous sequences, leading to their silencing as well. In such cells or organisms, use of pre-selected UiRNA targeted to a UtRNA in a chimeric RNA transcript should lead to the silencing of corresponding endogenous genes or gene families.

Figure 2:
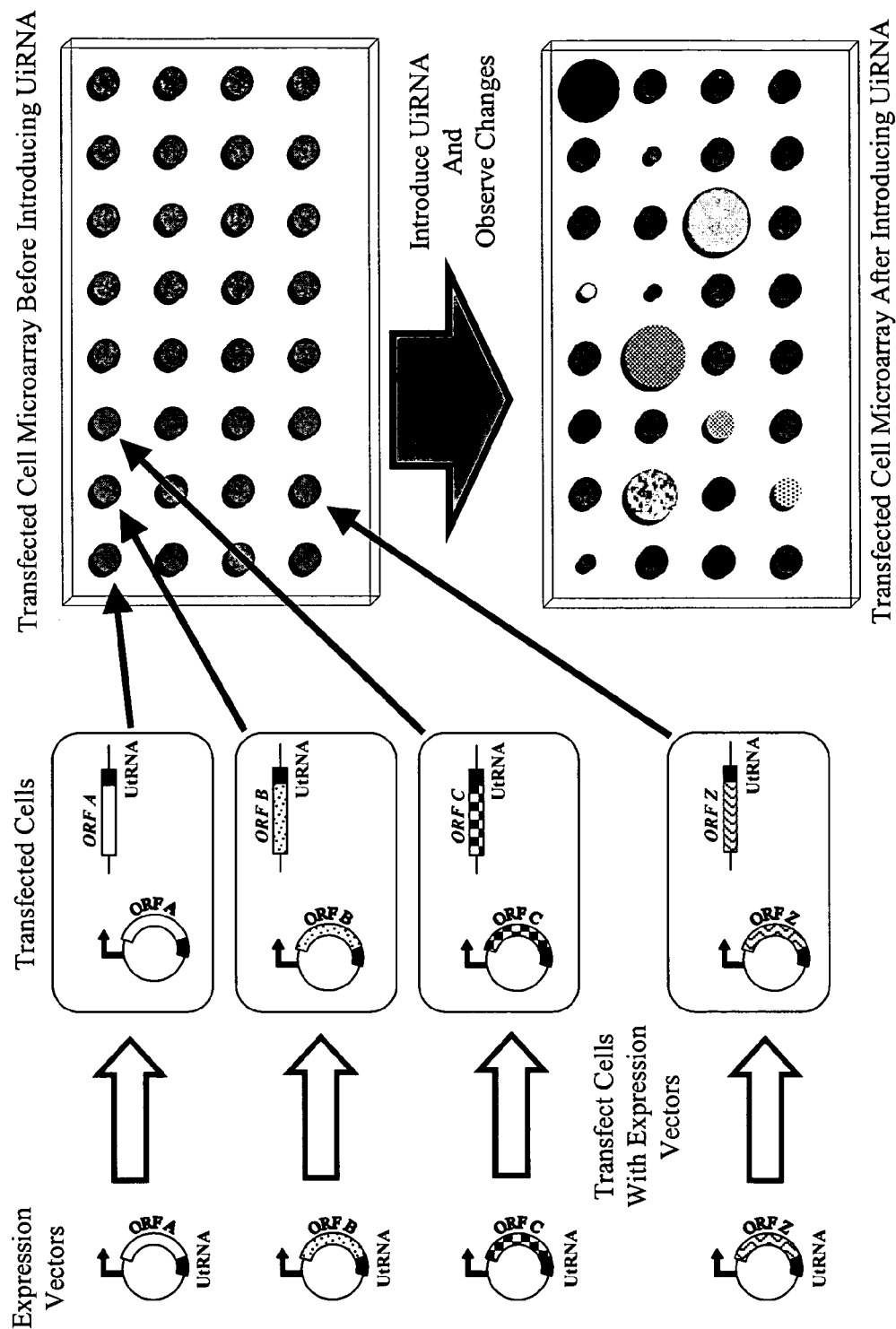
FIG. 2 depicts how the methods of the present invention can be used in an array-based format to target a plurality of gene products for RNAi with a single type of UiRNA, thereby simultaneously manipulating the expression levels of this plurality of gene products.

Since a single UtRNA can be incorporated into any number of chimeric RNA transcripts, and that UtRNA can be targeted by a single type of UiRNA, another significant advantage of the present invention is that the methods disclosed can be used to effectively manipulate the expression of a plurality of gene products. Such manipulation of expression of a plurality of gene products may be done either simultaneously or nonsimultaneously. Consequently, the methods of the present invention can be used to determine the effects of altered levels of expression of a plurality of gene products in a plurality of cells, or cell clusters or cultures, or organisms transfected with expression cassettes directing the expression of chimeric RNA transcripts bearing a common UtRNA, but encoding different gene products. Specifically, groups of transfected cells or organisms can be prepared, each group transfected with a different expression cassette that directs the expression of a specific chimeric RNA transcript encoding a unique gene product in a subject RNA, but bearing a common UtRNA. These groups of cells or organisms, each of which directs the overexpression of the particular gene product encoded by their expression cassette, can be treated with the same UiRNA to reduce the expression of these particular gene products (FIG. 2). Consequently, the method of the present invention provide a means for determining the effects of altered levels of expression of a plurality of gene products, using a single type of siRNA to promote RNAi-induced silencing of expression of the heterologous gene products encoded in the various chimeric RNA transcripts. Such groups of transfected cells or organisms can be cultured, split into a pair of cultures and one member of the pair can be treated with UiRNA. Cells or organisms from the treated and untreated paired cultures can then be compared to determine the effects of altered levels of expression of the particular gene product encoded by the expression cassette carried by those cells or organisms. The comparison of treated and untreated paired cultures can be by any means known to the art. Comparisons could, for example, involve comparing growth rates, comparing cellular morphologies, comparing the expression of specific cellular markers, or comparing the performance or behavior of the cells or organisms in specific diagnostic assays.

In preferred embodiments of the present invention the UtRNA employed can be designed to encode a readily detectable peptide, such as an epitope tag, fluorescent peptide, enzymatic tag, etc., such that, when cloned in-frame with a nucleotide sequence encoding a gene product whose expression is to be manipulated, the UtRNA directs the addition of the detectable peptide to the expressed gene product. The UtRNA encoding the detectable peptide can be added to either end of the sequence encoding the gene product to be manipulated so that the detectable peptide tag is added to one end or the other of the native gene product (FIG. 1). Alternatively, the UtRNA can be cloned within the sequence encoding the gene product to be manipulated, so that the detectable peptide tag is found imbedded within the natural polypeptide sequence of the gene product (FIG. 1). Preferably, and regardless of the location chosen for the detectable peptide tag encoded by the UtRNA and added to the polypeptide sequence of the gene product whose expression is to be manipulated, the detectable peptide tag added to the expressed gene product facilitates the ready detection, quantitation, and perhaps localization of the resulting expressed fusion protein. Hence, the detectable peptide tag can be exploited by researchers to track or follow not only the levels of expression of the recombinantly expressed fusion protein directed by the expression cassette in which it is encoded, but also can be used to track or follow the effects of treatment of such cells with corresponding UiRNAs, or control siRNAs. In other words, the detectable peptide tag present on a recombinantly expressed fusion protein allows researchers to readily assess whether the desired gene is being overexpressed at the protein level in transfected target cells before the introduction of UiRNA, and whether the expression of the protein is diminished or silenced following the introduction of, or treatment with, siRNAs.

On the other hand, the UtRNA need not necessarily be designed to encode a detectable peptide, and need not necessarily be cloned within, or directly adjacent to the coding region encoding the gene product whose expression is to be manipulated. The expression cassettes of the present invention may be designed and assembled such that the UtRNA ends up in the 5' untranslated region, or in the 3' untranslated region of the recombinant transcript encoding a gene whose expression is to be manipulated (FIG. 1). In essence, the location of UtRNA in the chimeric RNA transcript is a matter of choice, so long as the UtRNA allows for the effective targeting of the chimeric RNA transcript for RNAi-induced degradation of the subject RNA when cells (or organisms) are treated with UiRNAs of corresponding sequence.

Importantly, cell types or cell lines vary with respect to their basal levels of expression of a particular gene product or family of gene products. Clearly, the type or line of cells chosen for practicing the methods of the present invention will have a profound effect on the results one will attain using the methods of the present invention, since different cell types or cell lines exhibiting different basal levels of endogenous expression of various gene products can be employed to practice the methods of the present invention. Generally speaking, and for the purpose of practicing the methods of the present invention, all cell types can be grouped into one of two categories, based on whether the cells of that cell type or line express a particular gene product or not. All cell types can be further divided into one of two categories based on whether they exhibit transitive RNAi or not. As described above, transitive RNAi refers to the process whereby RNAi induced by an administered siRNA (the primary siRNA) leads to the secondary silencing of non-targeted transcripts, such as transcripts of homologous sequence. As will be seen, the methods of the present invention can be expected to have significantly different net effects with respect to the manipulation of expression of a particular gene product depending upon in which of the resulting four categories the cell type or line falls (i.e., (a) expressing a particular gene product from an endogenous gene, and not exhibiting transitive RNAi, (b) not expressing a particular gene product from an endogenous gene, and not exhibiting transitive RNAi, (c) expressing a particular gene product from an endogenous gene, and exhibiting transitive RNAi, and (d) not expressing a particular gene product from an endogenous gene, and exhibiting transitive RNAi). While not wishing to be bound by any theory, the methods of the present invention are particularly useful in cells and organisms that either naturally exhibit transitive RNAi, or are otherwise made to exhibit transitive RNAi. These four categories will be discussed separately below.

Figure 3:
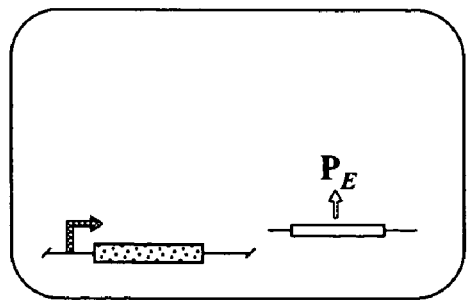
FIG. 3 illustrates how a UiRNA is used to target a chimeric RNA transcript for degradation in target cells expressing a corresponding endogenous transcript, wherein the target cells do not exhibit transitive RNAi.
Figure 3:
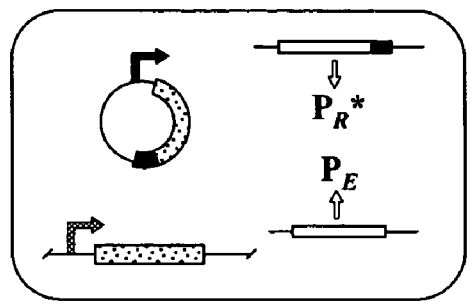
Figure 3:
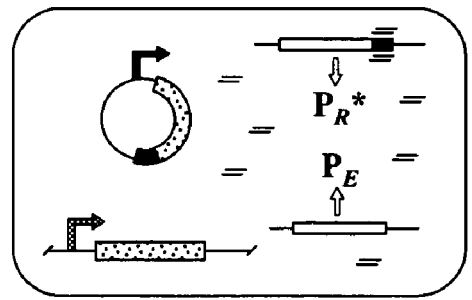
Figure 3:
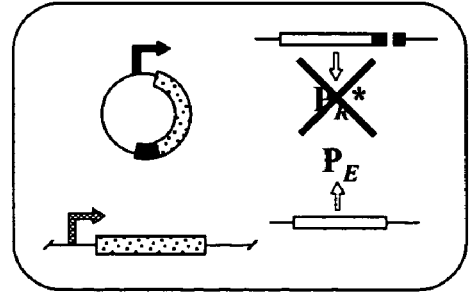

In the first category (FIG. 3), before transfection with an expression vector of the present invention, the cell type or cell line expresses a particular gene product (protein $P_E$) from an endogenous gene, but the cell does not exhibit transitive RNAi. Following transfection with an expression vector of the present invention, the transfected cells of the cell type or cell line express the gene product from both the endogenous gene (protein $P_E$), and from the chimeric RNA transcripts of the present invention (protein $P_R^*$). Following introduction of the UiRNA, which targets the UtRNA of the chimeric RNA transcript, expression of the gene product from the chimeric RNA transcripts of the present invention (protein $P_R^*$) is silenced, but expression of the gene product from the endogenous gene (protein $P_E$) continues. In this category, following the introduction of the UiRNA, the levels of expression of the gene product under study are not likely to drop below the initial level resulting from basal expression from the endogenous gene.

Figure 4:
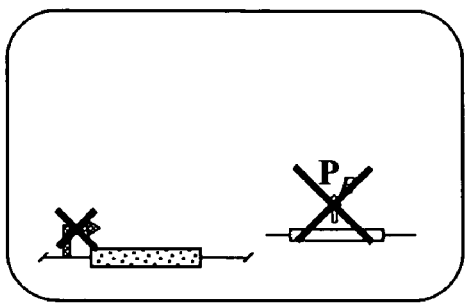
FIG. 4 illustrates how a UiRNA is used to target a chimeric RNA transcript for degradation in target cells that do not express a corresponding endogenous transcript, and wherein the target cells do not exhibit transitive RNAi.
Figure 4:
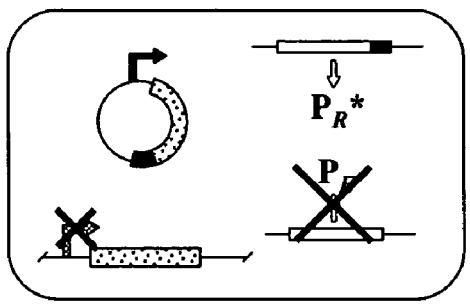
Figure 4:
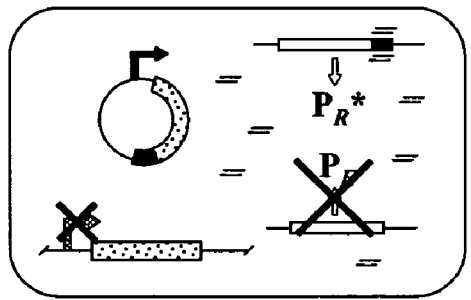
Figure 4:
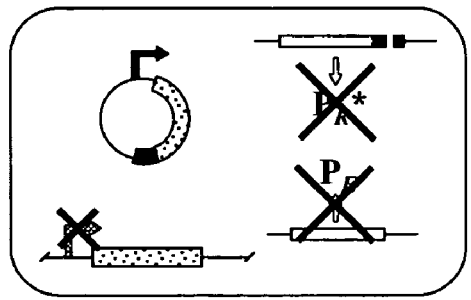

In the second category (FIG. 4), before transfection with an expression vector of the present invention, the cell type or cell line does not express a particular gene product (protein $P_E$) from an endogenous gene, and the cell does not exhibit transitive RNAi. Following transfection with an expression vector of the present invention, the transfected cells of the cell type or cell line express the particular gene product from the chimeric RNA transcripts of the present invention (protein $P_R^*$). Following introduction of the UiRNA, which targets the UtRNA of the chimeric RNA transcript, expression of the gene product from the chimeric RNA transcripts of the present invention (protein $P_R^*$) is silenced. In this category, following the introduction of the UiRNA, the levels of expression of the gene product under study will generally drop significantly below the maximum levels of expression directed by the transgene, but the amount by which the expression level is reduced will depend upon numerous factors.

Figure 5:
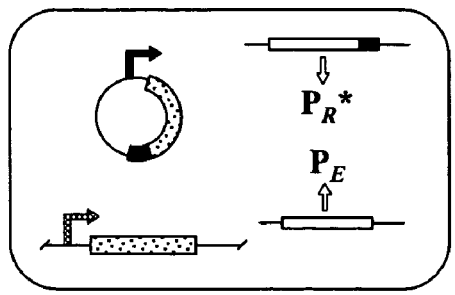
FIG. 5 illustrates how the methods of the present invention can be used to manipulate gene expression in target cells that express a chimeric RNA transcript, as well as a corresponding endogenous transcript, and also exhibit transitive RNAi.
Figure 5:
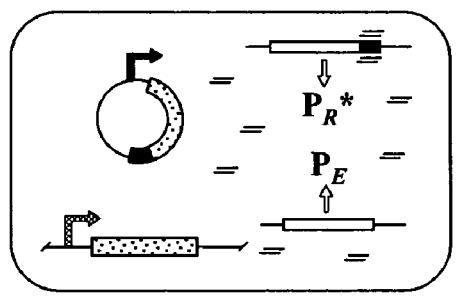
Figure 5:
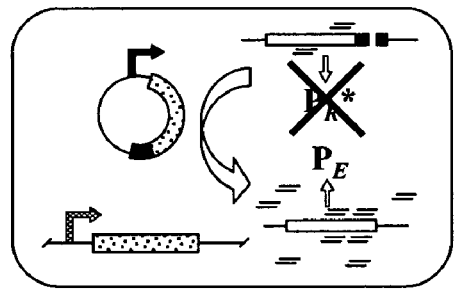
Figure 5:
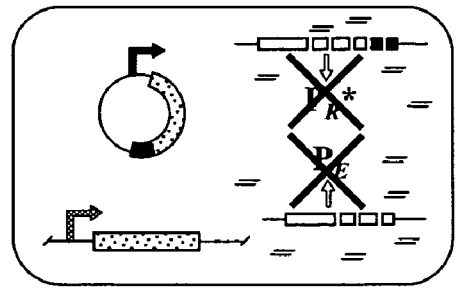

In the third category (FIG. 5), before transfection with an expression vector of the present invention, the cell type or cell line expresses a particular gene product (protein $P_E$) from an endogenous gene, and the cell exhibits transitive RNAi. Following transfection with an expression vector of the present invention, the transfected cells of the cell type or cell line express the gene product from both the endogenous gene (protein $P_E$), and from the chimeric RNA transcripts of the present invention (protein $P_{R*}$). Following introduction of the UiRNA, which targets the UtRNA of the chimeric RNA transcript, expression of the gene product from the chimeric RNA transcripts of the present invention (protein $P_{R*}$) is silenced, and secondary siRNAs generated during the primary RNAi response server to silence expression of the gene product from the endogenous gene. In this category, following the introduction of the UiRNA, the levels of expression of the gene product under study will generally drop significantly below the maximum levels of expression seen following transfection of the transgene, and likely will drop below the initial levels observed before the transfection of the transgene. How much below initial levels gene product expression will drop depends upon how effectively the silencing signal "transits" along the chimeric RNA transcript and to corresponding endogenous transcripts to induce a secondary RNAi response. Importantly, if the silencing signal transits efficiently to endogenous transcripts, and if the gene product under study is a member of a gene family, the secondary RNAi response may also lead to the silencing of expression of paralogous genes.

In the fourth category (not depicted), before transfection with an expression vector of the present invention, the cell type or cell line does not express a particular gene product (protein $P_E$) from an endogenous gene, but the cell does exhibit transitive RNAi. Following transfection with an expression vector of the present invention, the transfected cells of the cell type or cell line express the particular gene product from the chimeric RNA transcripts of the present invention (protein $P_{R*}$). Following introduction of the UiRNA, which targets the UtRNA of the chimeric RNA transcript, expression of the gene product from the chimeric RNA transcripts of the present invention (protein $P_{R*}$) is silenced. In this category, following the introduction of the UiRNA, the levels of expression of the gene product under study will generally drop significantly below the maximum levels of expression directed by the transgene, but the amount by which the expression level is reduced will depend upon numerous factors. As above, if the silencing signal can transit efficiently to endogenous transcripts, and if the gene product under study is a member of a gene family—other members of which are expressed in this cell type or line—then a secondary RNAi response may lead to the silencing of expression of paralogous genes.

Cells that naturally exhibit transitive RNAi include, but are not limited to the cells of *C. elegans* and plants. Other cells may be induced or enabled to exhibit transitive RNAi by, e.g., introducing into the cells exogenous genes encoding the machinery required for transitive RNAi. The expected results of methods of the present invention as described above for cells naturally exhibiting transitive RNAi are also expected to be obtained in cells that are made to exhibit transitive. The results expected from practicing the methods in such cell types (i.e., cells that do not normally exhibit transitive RNAi, but are made to do so) are identical to those described above for the third and fourth categories.

In another set of embodiments, the methods of the present invention provide kits for targeting a plurality of gene products for RNAi using a single UiRNA targeted to a common UtRNA. The methods of the present invention further provide kits for determining the effects of altered levels of expression of a plurality of gene products, or for assessing the involvement of a particular gene product, amongst a plurality of gene products, in pathogenicity, genetic disorders, and infectious diseases.

Typically, a kit should contain, in a carrier or compartmentalized container, reagents useful in any of the above-described embodiments of the invention. The carrier can be a container or support, in the form of, e.g., bag, box, tube, rack, and is optionally compartmentalized. The carrier may define an enclosed confinement for safety purposes during shipment and storage. Preferably, instructions for using a kit, and/or reagents contained therein, are also included in the kit.

In one set of kit embodiments, the kits of the present invention comprise one or more expression vectors that each comprise an expression cassette having a multiple cloning site and associated UtRNA, and an RNA that effectively directs RNAi of the recombinantly expressed gene products by targeting the UtRNA in chimeric RNA transcripts expressed from these expression cassettes. Using such kits, the nucleotide sequence encoding a particular gene product is conveniently cloned within the multiple cloning site of the expression vector, such that the resulting assembled vector directs the expression of a chimeric RNA transcript that comprises a nucleotide sequence encoding a particular gene product (the subject RNA) and the UtRNA. The RNA that is provided in the kits to direct the RNAi of the recombinantly expressed gene products by targeting the UtRNA, can be of any configuration that effectively directs RNAi by targeting the UtRNA, however, in a preferred embodiment the RNA is a single-stranded shRNA. In an alternative preferred embodiment the RNA is a double-stranded siRNA.

In another set of kit embodiments, the kits of the present invention comprise one or more expression vectors, as described above, plus a transcription vector that directs the in vivo transcription of an RNA that effectively directs the RNAi of expression of gene products by targeting the UtRNA borne by the chimeric RNA transcripts encoding the gene product whose expression is to be reduced. In a preferred embodiment this RNA is a single-stranded shRNA. In an alternative preferred embodiment, this RNA is a double-stranded siRNA.

Further provided by the methods of the present invention are gene product panel test kits designed to determine the effects of altered levels of expression of a plurality of gene products. In such kits a plurality of expression vectors, such as those described above, are provided, but these vectors are provided each with a different nucleotide sequence encoding a specific gene product inserted into it, such that the vector directs the transcription of a chimeric RNA transcript encoding a specific gene product (the subject RNA) and bearing a common UtRNA. Also provided in these gene product panel test kits would be either RNA that targets the UtRNA and induces RNAi, or a transcription vector that directs the expression of such an RNA. Preferably the RNA is either a small single-stranded hairpin RNA, or a double-stranded siRNA. Advantageously, these gene product panel kits include at least two expression vectors that direct the expression of different gene products, but the expression of all gene products encoded in the supplied vectors can be reduced by introducing an RNA designed to promote RNAi by targeting the UtRNA in the chimeric RNA transcripts encoded in the supplied vectors (i.e., a UiRNA). Preferably these gene product panel test kits contain at least 2, 3, 4, 6, 8, 12, 16, 24, 32, 36, 40, 48, 56, 60, 64, 72, 80, 84, 88, 96 or 160, 240, 360, 400, 480, 560, 600, 1000 or more such expression vectors, each capable of directing the expression of a different gene product, and directing the production of a chimeric RNA transcript comprising a UtRNA and the nucleotide sequence encoding a specific gene product (the subject RNA).

Beneficially, the expression vectors of these gene product panel test kits can encode different human gene products that are related in sequence or function (i.e., drug metabolizing enzymes, such as mixed function oxidases, cytochrome P450 enzymes, and the like), or are involved in a single metabolic pathway, or represent a collection of interacting proteins that are associated with a particular genetic disorder or infectious disease.

Alternatively, the expression vectors of these gene product panel test kits may encode different gene products from a human pathogen (e.g., viral genes from a human viral pathogen, or virulence factor genes from a human parasite), or the expression vectors may encode gene products from a human pathogen that are required for infection of, or maintenance within, a non-human species that serves as a vector or reservoir for the disease (e.g., transmission factor genes of arboviruses or parasitic protozoa such as *Plasmodium falciparum*). Also, the expression vectors of these gene product panel test kits may encode different gene products from non-human species that serve as vectors for transmission of infectious diseases (e.g., genes known or suspected to be required for infection of *Aedes aegypti* mosquitoes by West Nile virus).

Further, the expression vectors included in a gene product panel test kit may be designed for producing the chimeric RNA transcripts of the present invention in human cells, or in the cells of non-human species that serve as vectors for transmission of infectious diseases.

Alternatively, the expression vectors included in a gene product panel test kit may be designed for producing the chimeric RNA transcripts of the present invention in plant cells. Innumerable such gene product panel test kits utilizing the methods of the present invention can be envisioned by skilled artisans appraised of the present invention, and the examples provided above are not meant to limit the design or application of such kits.

In yet another set of embodiments, the methods of the present invention provide for arrays designed to utilize RNAi to either simultaneously manipulate levels of expression of a plurality of gene products, or simultaneously determine the effects of altered levels of expression of a plurality of gene products all by using a single siRNA. For these embodiments, the methods of the present invention provide for a transfection array of DNA expression vectors, where the expression vectors at different addresses within the array are capable of directing the production of different chimeric RNA transcripts that have different subject RNAs to be degraded, but bear a common UtRNA. The methods of the present invention further provide for arrays of transfected cells, wherein collections of cells at specific addresses within the array are transfected with a particular DNA expression vector, and this vector directs the production of a chimeric RNA transcript that encodes a particular gene product but bears a common UtRNA. In this manner, arrays of cells showing altered levels of expression of a plurality of particular gene products are formed, but a single siRNA can be used to induce RNAi and thereby diminish expression of all gene products encoded by the chimeric RNA transcripts, by introducing into the cells a UiRNA, which corresponds to, and is capable of targeting, the UtRNA common to all of the chimeric RNA transcripts expressed within the cells of the array.

Such arrays can be microarrays of transfected cells or macroarrays of cultures of transfected cells. Such arrays can also be macroarrays of organisms expressing the chimeric RNA transcripts of the present invention. Examples of the organisms include nematodes and plants. Nematode and plant cells, tissues, or plant seeds can also be used in the arrays. For the microarrays, the reverse transfection methods described by Sabatini in U.S. Pat. No. 6,544,790, which is incorporated by reference herein in its entirety, can be used to prepare either the transfection microarrays of expression vectors, or the microarrays of reverse transfected cells) of these embodiments.

Kits including one or more of the arrays of the present invention and a UiRNA are also contemplated.

Using these embodiments of the present invention (i.e., microarrays of reverse transfected cells, or macroarrays of transfected cells or organisms) the levels of expression of a plurality of gene products may be simultaneously manipulated as required. Initially, and in the absence of UiRNA, all gene products encoded in the chimeric transcripts of the present invention should be overexpressed to some degree. The degrees to which the gene products are overexpressed can be influenced by any means know in the art. For example, different constitutive promoters, exhibiting particular levels of transcriptional activity, can be incorporated into the expression cassettes of the present invention. Promoters exhibiting high transcriptional activity should lead to higher levels of initial overexpression. Alternatively, inducible or derepressible promoters can be incorporated into the expression cassettes of the present invention. Such promoters, which are well known in the art, can be manipulated by addition of particular inducing or repressing agents to the cell culture medium in order to intentionally alter their levels of transcriptional activity. Once appropriate levels of expression of the plurality of gene products under study are achieved, the levels of expression of the plurality of gene products can be conveniently and simultaneously diminished by the introduction of a single type of siRNA (UiRNA). Introduction of UiRNA corresponding in sequence to the UtRNA found in all chimeric RNA transcripts encoding the gene products under study, induces RNAi, and it's associated silencing (reduction) of expression of all gene products being expressed from the chimeric RNA transcripts of the present invention. The introduction of UiRNA can be by any means, but the means chosen, as well as the amount introduced, and the nature of the UiRNA and corresponding UtRNA, will determine the amount and duration of silencing (reduced expression) observed.

Whatever the means of introduction of UiRNA, the methods of the present invention provide a means to "silence," or generally diminish expression, all of the gene products expressed by the cells of the array. This allows the cells clusters at specific addresses in the array to be compared under conditions of increased expression of a particular gene product (in the absence of a UiRNA), and decreased expression of a particular gene product (in the presence of UiRNA). Since the expression levels of the plurality of gene products expressed within the cells of the array can be manipulated simultaneously and conveniently by a uniform treatment (i.e., the introduction of UiRNA), the methods of the present invention are particularly useful for the high-throughput analysis of gene function, in which large sets of DNAs are screened to identify those DNAs encoding gene products that cause cellular phenotypes of interest, or exhibit other properties of interest.

Importantly, as described above, cell types or cell lines vary with respect to their basal levels of expression of a particular gene product or family of gene products. Clearly, the type or line of cells chosen for practicing the methods of the present invention will have a profound effect on the results attained, since different cell types or cell lines exhibiting different basal levels of endogenous expression of various gene products can be employed to make the microarrays and macroarrays just described. Generally speaking, and for the purpose of practicing the methods of the present invention, all cell types can be grouped into one of four categories, based on whether the cells of that cell type or line express a particular gene product or not, and whether they exhibit transitive RNAi or not. As described above, the methods of the present invention can be expected to have different net effects with respect to the manipulation of expression of a particular gene product depending upon in which of these four categories the cell type or cell line falls.

In another set of embodiments, the methods of the present invention provide a means to reduce the expression of endogenous genes in organisms or cells that either naturally exhibit transitive RNAi, or are made to do so. In these embodiments, the coding region of the endogenous gene whose expression is desired to be reduced is cloned within an expression cassette that also includes a UtRNA and the expression cassette is included in an expression vector. The coding region is inserted into the expression cassette so that the cassette directs the expression of a chimeric RNA transcript, comprising the nucleotide sequence encoding the gene product of interest (the subject RNA) and a UtRNA, adjacent to the coding region. For example, if designed to encode a peptide, the UtRNA can be cloned in-frame with the 3' end of the coding region, so that the UtRNA directs the addition of a peptide tag to the carboxyl-terminus of the gene product. Alternatively, the UtRNA may be cloned just downstream of the stop codon, in the 3' UTR. The resulting expression vector is then transfected into cells exhibiting transitive RNAi. Once transfected, these cells express the chimeric RNA transcript bearing the UtRNA. When reduction of endogenous expression is desired, a UiRNA corresponding in sequence to the UtRNA is introduced into the cell. This UiRNA serves as a primary siRNA that induces a primary RNAi response by targeting the UtRNA in the chimeric RNA transcript. During the primary RNAi response, secondary siRNAs are generated corresponding to sequences 5' of the UtRNA and in the region encoding the endogenous gene product. These secondary siRNAs promote RNAi-induced silencing of the sequences to which they correspond; namely the coding region 5' to the UtRNA. Because the sequences that these secondary siRNAs target are common to transcripts from both recombinantly-expressed and endogenously-expressed genes, a secondary RNAi response induced by these secondary siRNAs leads to reduced expression of gene products encoded by both recombinant and endogenous transcripts. Hence, the methods of the present invention can be used in any cell or organism exhibiting transitive RNAi, whether naturally exhibited or otherwise induced, to reduce the expression of any gene product from endogenous transcripts.

Advantageously, the methods of the present invention can also be used to reduce the expression of highly similar or homologous gene products. It is known from experiments conducted in organisms and cells exhibiting transitive RNAi, that siRNAs targeted to a particular member of a gene family can ultimately induce silencing of other members of that same gene family. The mechanism by which this transitive secondary silencing occurs is thought to involve the generation of secondary siRNAs corresponding to nucleotide sequences outside of the region of nucleotide sequences in transcripts originally targeted by the primary (i.e., introduced) siRNAs. (In *C. elegans*, these secondary siRNAs correspond to nucleotide sequences 5' of the nucleotide sequence targeted by the primary siRNA, but in plants the secondary siRNAs correspond to nucleotide sequences both 5' and 3' of the originally nucleotide targeted sequence.) If these secondary siRNAs correspond to sequences that are shared by gene family members, these secondary siRNAs will also target these gene family members for silencing during a secondary RNAi response. However, in order for gene family members to be targeted by secondary siRNAs, they must possess regions of sequence that are identical to, or very similar to, regions of sequence adjacent to the sequence targeted by the original primary siRNAs.

The advantages to using the methods of the present invention, in the manner described above, to reduce expression of endogenous genes in cells and organisms exhibiting transitive RNAi, are at least two-fold. First, if a particular UtRNA is incorporated into a plurality of chimeric RNA transcripts, a single type of siRNA that targets that that UtRNA (a UiRNA) can be used to reduce the expression of all gene products encoded in that plurality of chimeric RNA transcripts. Second, the UtRNA targeted by the UiRNA, and the UiRNA employed, can be selected and tested in advance, in order to assure that UiRNA-mediated gene silencing works effectively and without regard to the nature of the gene product coding sequence included within the chimeric RNA transcripts.

Importantly, however, in order for these embodiments to take advantage of the phenomenon of transitive RNAi to affect silencing of homologous messages, the UtRNA must be situated adjacent to, and preferably nearby, the nucleotide sequence encoding the gene product whose expression is to be reduced or silenced. Advantageously, the UtRNA can either be inserted into the 3' untranslated region just 3' of the stop codon, or, if made to encode a peptide, can be cloned in frame with the 3' end of the coding region for the gene product such that the chimeric RNA transcript produced from the expression cassette encodes a fusion protein. In the latter case, it is preferable for the peptide encoded by the UtRNA to be a peptide, which can be used for the ready detection and quantitation of the expressed fusion protein.

In still another set of embodiments, the methods of the present invention provide a method of treating disease in organisms or cells that naturally exhibit transitive RNAi (i.e., nematodes and plants), or in organisms or cells that are made to perform transitive RNAi. In these embodiments, an expression cassette directing the expression of a chimeric RNA transcript, comprising a nucleotide sequence encoding a disease-related protein (as the subject RNA) and a UtRNA, is introduced into the cells, or organism in need of treatment. The expression cassette introduced directs the production of a chimeric RNA transcript, which bears the subject RNA and the UtRNA. At some point in time when a reduction in the level of expression of the disease-related protein is desired, a UiRNA, which corresponds in sequence to the UtRNA, is introduced into the cells or organism to promote a reduction of expression of the recombinantly expressed gene-product through a primary RNAi response. During the course of the primary RNAi response secondary siRNAs are produced that will correspond to sequences adjacent to, or just upstream (5') of the UtRNA. These secondary siRNAs induce a secondary RNAi response that results in the reduction of expression or silencing of both recombinantly expressed and endogenously expressed gene product. The net reduction of expression of both recombinantly expressed and endogenously expressed gene product, desirably promotes an improvement in the disease state.

In a final set of embodiments, the methods of the present invention provide a method of treating an infectious disease caused by a pathogenic organism that naturally exhibits transitive RNAi. In these embodiments, transitive RNAi is used to silence, or significantly reduce, expression of a critical gene product (e.g., a virulence factor) in the pathogenic organism. Examples of pathogenic organisms exhibiting transitive RNAi include nematode worms, which result in a variety of diseases in agricultural crops and livestock, and possibly protozoa, such as trypanosomes, which cause a variety of diseases (i.e., sleeping sickness) in humans and domesticated animals.

3. Expression Cassettes

It will be apparent to skilled artisans that any molecular genetic engineering methods or recombinant DNA technologies may be used in the present invention for purposes of preparing the expression cassettes and expression vectors of the present invention. Generally, once prepared, a nucleic acid encoding an expression cassette can be incorporated into an expression vector or a delivery vector, which is introduced to a suitable target cell.

The expression cassettes employed in the various embodiments described above can be of any suitable construction, and can be included in any appropriate delivery vector. Such delivery vectors include plasmid DNA, viral DNA, and the like. The means by which the expression cassette in its delivery or expression vector is introduced into target cells or target organism can be transfection, reverse transfection, virus induced transfection, electroporation, direct introduction by biolystics (e.g., using a "gene gun;" BioRad, Inc., Emeryville, Calif.), and the like. Other methods that can be employed include methods widely known in the art as the methods of gene therapy. Once delivered into a target cell, or target organism the expression cassette may be maintained on an autonomously replicating piece of DNA (e.g., an expression vector), or may be integrated into the genome of the target cell or target organism.

Typically, to assemble the expression cassettes and vectors of the present invention a nucleic acid, preferably a DNA, encoding a gene product under study is incorporated into a unique restriction endonuclease cleavage site, or a multiple cloning site, within a pre-existing "empty" expression cassette bearing a UtRNA-encoding sequence to form a complete recombinant expression cassette that is capable of directing the production of the chimeric RNA transcripts of the present invention. These chimeric RNA transcripts comprise a subject RNA, generally encoding a specific gene product, and the UtRNA, which can be targeted by a corresponding UiRNA, to induced the RNAi-mediated degradation of the chimeric RNA transcript. Frequently such complete recombinant expression cassettes reside within, or inserted into, expression vectors designed for the expression of such chimeric RNA transcripts, and recombinant proteins. Many types of vectors can be used for the present invention to produce chimeric RNA transcripts bearing UtRNAs. Methods for the construction of an expression vector for purposes of this invention should be apparent to skilled artisans apprised of the present invention. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

4. Expression Vectors

Generally, the expression cassettes inserted or assembled within the expression vectors have a promoter operably linked to a DNA encoding the subject RNA that is to be manipulated, plus a UtRNA. The promoter can be a native promoter, i.e., a promoter that is responsible for the expression of that particular gene product in cells, or it can be any other suitable promoter. Alternatively, the expression cassette can be a chimera, i.e., having a heterologous promoter that is not the native promoter responsible for the expression of the gene product whose expression is to be manipulated. Such heterologous promoters can even be from a different species than the target cell or organism.

The expression vector may further include an origin of DNA replication for the replication of the vectors in target cells. Preferably, the expression vectors also include a replication origin for the amplification of the vectors in, e.g., *E. coli*, and selection marker(s) for selecting and maintaining only those target cells harboring the expression vectors. Additionally, the expression vectors preferably also contain inducible or derepressible promoters, which function to control the transcription of the chimeric RNA transcript from the DNA that encodes it. Other regulatory sequences such as transcriptional enhancer sequences and translation regulation sequences (e.g., Shine-Dalgarno sequence) can also be operably included in the expression vectors. Transcription termination sequences, and polyadenylation signal sequences, such as those from bovine growth hormone, SV40, lacZ and AcMNPV polyhedral protein genes, may also be operably linked to the DNA encoding the gene product whose expression is to be manipulated.

As mentioned above, the UtRNA, which is also included in the expression vector, may be situated in any of the five possible locations, with respect to the subject RNA whose cellular concentration is to be manipulated, or with respect to the coding sequence of the gene product whose expression is to be manipulated, as depicted in FIG. 1. In all cases the subject RNA is operably linked to the UtRNA, such that the resulting chimeric RNA transcript is subject to the RNAi-induced degradation when targeted by an introduced UiRNA that corresponds in nucleotide sequence to the nucleotide sequence of the UtRNA. If the particular embodiment of the invention to be practiced exploits transitive RNAi to induce the silencing of endogenous or homologous transcripts, and the transitive RNAi takes place within a nematode, or nematode cell, the coding sequence is preferably placed 5' of the UtRNA, in one of two possible configurations. In the first of these two possible configurations, the UtRNA, which is situated adjacent to the coding region, is designed to encode a peptide sequence, and is placed in frame with the 3' end of the coding sequence. In the second, the UtRNA is placed in the 3' untranslated region, just downstream (or 3') of the stop codon. If the particular embodiment of the invention to be practiced exploits transitive RNAi to induce the silencing of endogenous or homologous transcripts, and the transitive RNAi takes place within a plant, or plant cell, the UtRNA can be placed in any location within the chimeric RNA transcript, as long as it is operably linked to the subject RNA.

In a preferred embodiment the UtRNA encodes a detectable peptide, and is operably linked to the subject RNA by being placed in frame with the 3' end of the coding sequence, such that the expressed chimeric RNA transcript ultimately results in the translation of a fusion protein with a carboxyl-terminal detectable peptide tag.

5. Detectable Peptide Tags

As mentioned above, the UtRNA can encode an detectable peptide tag that facilitates detection of an expressed fusion protein bearing that tag. The tag may be an epitope tag that is useful for immunodetection, quantitation, and possibly the purification of the gene product under study. Such a UtRNA can be operably linked to the DNA encoding the gene product whose expression is to be manipulated such that a fusion protein bearing the epitope tag is expressed. Examples of useful epitope tags include, but are not limited to, influenza virus hemagglutinin (HA), Simian Virus 5 (V5), polyhistidine (His6), c-myc, FLAG™, and the like. Specific antibodies immunoreactive with these epitope tags, and many others, are commercially available. Additionally, proteins expressed as fusions with polyhistidine tags can be easily detected and/or purified with, e.g., $Ni^{2+}$ affinity columns.

If the UtRNA of the present invention is designed to encode an epitope tag and is cloned in frame with the nucleotide sequence encoding the gene product whose level of expression is to be manipulated, the resulting fusion protein can be readily detected by Western blotting. Also, the addition of an epitope tag allows the expression level or concentration of the resulting fusion protein to be determined in a sample, such as a cell lysate, without the need for separation, isolation or purification. For this purpose, it is preferred that an antibody selectively immunoreactive with the epitope tag is used in an immunoassay. For example, immunocytochemical methods can be used. Other well known antibody-based techniques can also be used including, e.g., enzyme-linked immunosorbent assay (ELISA), radioimmunoassay (RIA), immunoradiometric assays (IRMA), fluorescent immunoassays, protein A immunoassays, and immunoenzymatic assays (IEMA). See e.g., U.S. Pat. Nos. 4,376,110 and 4,486,530, both of which are incorporated herein by reference. These antibody-based techniques are widely known in the art and are described readily available references, such as Using Antibodies: A Laboratory Manual (Harlow, Cold Spring Harbor Press (1999)).

Alternatively, the UtRNA can encode any other type of detectable peptide, including, but not limited to, fluorescent peptides, or peptides exhibiting enzymatic activity. For example, the UtRNA can encode enhanced green fluorescent protein, or any other variety of fluorescent protein. Preferably, such fluorescent peptides allow for the ready detection of expression of fusion proteins bearing them, and even more preferably, they allow for the quantitation of such fusion proteins. Examples of such fluorescent peptides are widely known in the art, and protocols for their detection and quantitation are available from a variety of sources.

Examples of peptides exhibiting enzymatic activity are also widely known in the art. Such peptides include, but are not limited to, alkaline phosphatase, horseradish peroxidase, and β-galactosidase, which allow for the ready detection and quantitation of fusion proteins bearing them using specific enzymatic assays. Examples of such peptides exhibiting enzymatic activity are widely known in the art, and protocols for their detection and quantitation are available from a variety of sources.

6. Additional Features

The expression vectors or the present invention may also contain components that direct the recombinantly expressed gene product or fusion protein to the surface of the cell, to a particular intracellular compartment, or to be secreted, as required. Signal peptides, nuclear localization sequences, endoplasmic reticulum retention signals, mitochondrial localization sequences, myristoylation signals, palmitoylation signals, and transmembrane sequences are examples of optional components that can determine the destination of expressed gene products. When it is desirable to manipulate the expression of two or more gene products in a single host cell by RNAi, two expression cassettes directing the expression of two different chimeric RNA transcripts, each encoding a single gene product, in a distinct subject RNA that is operably linked to a UtRNA, may be incorporated into a single vector. Alternatively, the two expression cassettes may reside within two distinct expression vectors, both of which are introduced into a single target cell. Advantageously, in either scenario, the same UtRNA may be included in both expression cassettes so that the same UiRNA can be used to reduce their expression. Alternatively, a different UtRNA can be incorporated into each expression cassette so that the expression of the two different gene products can be manipulated independently.

The expression vectors of the present invention can be introduced into the target cells by any techniques known in the art, e.g., by direct DNA transformation, microinjection, electroporation, viral infection, lipofection, biolystics, and the like. The expression of the gene products to be manipulated may be transient or stable, inducible or derepressible. The expression vectors can be maintained in target cells in an extrachromosomal state, i.e., as self-replicating plasmids or viruses. Alternatively, the expression vectors, or portions thereof, can be integrated into chromosomes of the target cells by conventional techniques such as site-specific recombination or selection of stable cell lines. In stable cell lines, at least the expression cassette portion of the expression vector is integrated into a chromosome of the target cells.

The vector construct can be designed to be suitable for expression in various target cells, including but not limited to bacteria, yeast cells, plant cells, nematode cells, insect cells, and mammalian and human cells. Methods for preparing expression vectors designed for expression of gene products in different target cells are well known in the art.

7. Introduction of UiRNA

A universal interfering RNA, or UiRNA, can be introduced into the transfected target cells of the present invention either exogenously, i.e., from outside the target cells, or endogenously, from transcription cassettes that direct the transcription of UiRNAs within the target cells. For exogenous introduction, the UiRNAs of the present invention are synthesized in vitro and introduced by transfection, lipofection, electroporation, or any other appropriate means. Such in vitro synthesized UiRNAs may be synthesized by chemical means, or by enzymatic means from the appropriate precursors. In addition, these in vitro synthesized UiRNAs may take different forms. They may be double-stranded RNA duplexes consisting of two annealed strands of about 21 nucleotides that form about 19 basepairs between them and have 3' overhangs of two nucleotides (Elbashir et al., *EMBO J.* 20:6877-6888 (2001) & Chiu and Rana, *Molec. Cell* 10:549-561 (2002)). Alternatively, these in vitro synthesized UiRNAs may be single-stranded short hairpin RNAs (Sui et al., *Proc. Natl. Acad. Sci. U.S.A.* 99:5515-5520 (2002); Yu et al., *Proc. Natl. Acad. Sci. U.S.A.* 99:6047-6052 (2002); and Paul et al., *Nature Biotech.* 20:505-508 (2002)).

For endogenous introduction, UiRNAs are transcribed within the target cells of the present invention. Such UiRNAs can be of any appropriate form, but are preferably transcribed as small hairpin RNAs that are processed to for active UiRNAs by cellular nucleases. Transcription cassettes directing the expression of UiRNAs, like the expression cassettes directing the expression of chimeric RNA transcripts, described above, can be incorporated into a transcription vector or a delivery vector, which is introduced to a suitable target cell.

The expression cassettes employed for the in vivo transcription of UiRNA can be of any suitable construction, and can be included in any appropriate delivery vector. Such delivery vectors include plasmid DNA, viral DNA, and the like. The means by which the UiRNA expression cassette in its delivery or expression vector is introduced into target cells or target organism can be transfection, reverse transfection, virus induced transfection, electroporation, direct introduction by biolystics (e.g., using a "gene gun;" BioRad, Inc., Emeryville, Calif.), and the like. Other methods that can be employed include methods widely known in the art as the methods of gene therapy. Once delivered into a target cell, or target organism the UiRNA expression cassette may be maintained on an autonomously replicating piece of DNA (e.g., an expression vector), or may be integrated into the genome of the target cell or target organism.

Typically, to assemble the UiRNA expression cassettes and vectors of the present invention a nucleic acid encoding the UiRNA, or a UiRNA precursor such as an shRNA, is operably linked to a promoter sequence that directs the transcription of the encoded interfering RNA, or interfering RNA precursor, by an RNA polymerase. Preferably, the promoter used in the UiRNA expression cassette is inducible or derepressible and tightly regulated, such that the expression of the UiRNA can be readily controlled. RNA transcription cassettes and vectors suitable for use in the methods of the present invention are known in the art and have been described in a variety of references. For example, methods for the in vivo expression of shRNAs are presented in U.S. Patent Application Nos. 2003/0068821, 2003/0139363 and 2003/0144232, which are incorporated herein by reference, in their entirety. Methods for the stable expression of interfering RNAs have also been described in papers by Brummelkamp, et al., (*Science* 296: 550-553 (2002)), Paddison, et al., (*Genes and Dev.* 16:948-958 (2002)), Sui et al., (*Proc. Natl. Acad. Sci. U.S.A.* 99:5515-5520 (2002)), and Xia, et al., (*Nucleic Acids Res.* 31:e100 (2003)), which are all incorporated herein by reference in their entirety. Additionally, methods for the establishment of conditional transcription vectors expressing interfering RNAs in mammalian cells were recently described in a paper by Matsukura et al., (*Nucleic Acids Res.* 31:77 (2003)), which is also incorporated herein by reference in its entirety. Finally, a chemical-regulated inducible interfering RNA expression system that functions in plants has recently been described in a paper by Guo, et al., (*Plant J.* 34:383-392 (2003)), which is also incorporated herein by reference in its entirety.

General methods for the construction of such interfering RNA transcription cassettes and vectors should be apparent to skilled artisans apprised of the present invention. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

8. Gene Therapy Techniques

Generally, gene therapy techniques can be used to introduce either the expression cassettes or vectors of the present invention containing DNA sequences that direct the production of UiRNAs, or their precursors, or both. Additionally, gene therapy techniques can be used to introduce DNAs that direct the transcription of RNAs (i.e., transcription cassettes) that either function as UiRNAs, or serve as precursors (i.e., shRNAs) that are processed into UiRNAs by cellular enzymes. In one set of embodiments, the levels of expression of a plurality of gene products is manipulated in cells, tissue, organisms or patients using UiRNAs targeted to the UtRNAs residing in chimeric RNA transcripts transcribed from expression cassettes introduced by a gene therapy approach. For example, nucleic acids that direct the production of a plurality of chimeric RNA transcripts encoding a plurality of gene products, or portions or fragments thereof, and bearing a UtRNA, are introduced into cells, tissues, organisms or patients such that the chimeric RNA transcripts are expressed from expression cassettes provided by the introduced nucleic acids. Subsequently, or simultaneously, UiRNAs are introduced into the same cells, tissues, organisms or patients by any of the means described above. These UiRNAs target the UtRNAs of the chimeric RNA transcripts and reduce the expression of the encoded gene product by directing the degradation of these transcripts. For these purposes, nucleic acids encoding a particular gene product, or portions or fragments thereof, and bearing a UtRNA, especially a UtRNA located 3' of the coding sequence, can be used in the gene therapy approaches in accordance with the present invention. These embodiments are inherently useful if manipulation of levels of expression of gene products encoded by, and expressed from, transgenes is required. Additionally, in cells, tissues, organisms or patients that naturally exhibit transitive RNAi, or are made to exhibit transitive RNAi, the methods of the present invention can also be used to reduce expression from corresponding endogenous genes, and/or homologous genes.

In cells, tissue, organisms and patients not exhibiting transitive RNAi, the methods of the present invention can be used for gene therapy as follows: if a disease-causing mutation exists an organism or patient or in an endogenous protein gene in cells or tissue in vitro, and if expression of a non-mutant form of that gene product is desirable, then a nucleic acid bearing an expression cassette that directs the production of a chimeric RNA transcript, including the coding region for the non-mutant protein and a UtRNA, can be introduced into the cells, tissues, organism or patient. The expression cassette can then be used to produce a chimeric RNA transcript within the cells, tissues or patient, and the levels of expression of the non-mutant gene product from chimeric RNA transcripts can be further manipulated, by the introduction of UiRNA that is directed to the UtRNA of the chimeric RNA transcripts. Advantageously, the expression cassette of the present invention can be integrated into the genome, and perhaps can be used to replace a corresponding defective endogenous gene by, e.g., homologous recombination. See U.S. Pat. No. 6,010,908, which is incorporated herein by reference. Alternatively, if the disease-causing mutation is a recessive mutation, the expression cassette is simply used to express a wild-type protein from a chimeric RNA transcript, and levels of expression of the wild-type protein can be manipulated as required by RNAi induced by introduced UiRNAs that target a UtRNA in the chimeric RNA transcript. In another embodiment, if the endogenous genes are non-mutant but the level of expression of the protein encoded thereby is desired to be increased, the expression cassette of the present invention, encoding the same gene product and bearing a UtRNA can be introduced into the patient by gene therapy. Once the expression cassette of the present invention is introduced, the level of expression of the desired gene product can be further manipulated (i.e., "fine-tuned") by the introduction of UiRNAs targeting the UtRNA borne by the chimeric RNA transcripts expressed from the expression cassettes.

Various gene therapy methods are well known in the art. Successes in gene therapy have been reported recently. See e.g., Kay et al., Nature Genet., 24:257-61 (2000); Cavazzana-Calvo et al., Science, 288:669 (2000); and Blaese et al., Science, 270: 475 (1995); Kantoff, et al., J. Exp. Med. 166:219 (1987).

Any suitable gene therapy methods may be used for the purposes of the present invention to direct the in vivo production of chimeric RNA transcripts bearing UtRNAs and encoding desired gene products. Generally, a nucleic acid encoding a desirable gene product and a functionally linked UtRNA are incorporated into a suitable expression vector and are operably linked to a promoter in the vector. Suitable promoters include but are not limited to viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Where tissue-specific expression of the chimeric RNA transcript and encoded gene product is desirable, tissue-specific promoters may be operably linked to the exogenous gene. In addition, selection markers may also be included in the vector for purposes of selecting, in vitro, those cells that contain the exogenous gene. Various selection markers known in the art may be used including, but not limited to, e.g., genes conferring resistance to neomycin, hygromycin, zeocin, and the like.

In one embodiment, an transcription cassette directing the transcription of the UiRNA, or a precursor thereof, is incorporated into a plasmid DNA vector, which is then introduced into target cells, tissues, organisms or patients. Many commercially available expression vectors may be useful for the present invention, including, e.g., pCEP4, pcDNAI, pIND, pSecTag2, pVAX1, pcDNA3.1, and pBI-EGFP, and pDisplay.

Various viral vectors may also be used for the methods of the present invention. Typically, in a viral vector, the viral genome is engineered to eliminate the disease-causing capability of the virus, e.g., the ability to replicate in the target cells. The exogenous nucleic acid to be introduced into cells or tissue in vitro or into a patient may be incorporated into the engineered viral genome, e.g., by inserting it into a viral gene that is non-essential to viral infectivity. Viral vectors are convenient to use as they can be easily introduced into cells, tissues and patients by way of infection. Once in the host cell, the recombinant viral genome is typically is integrated into the genome of the host cell. In rare instances, the recombinant viral genome may replicate autonomously and remain as an extrachromosomal elements.

A large number of retroviral vectors have been developed for gene therapy. These include vectors derived from oncoretroviruses (e.g., MLV), lentiviruses (e.g., HIV and SIV) and other retroviruses. For example, gene therapy vectors have been developed based on murine leukemia virus (See, Cepko, et al., Cell, 37:1053-1062 (1984), Cone and Mulligan, Proc. Natl. Acad. Sci. U.S.A., 81:6349-6353 (1984)), mouse mammary tumor virus (See, Salmons et al., Biochem. Biophys. Res. Commun., 159:1191-1198 (1984)), gibbon ape leukemia virus (See, Miller et al., J. Virology, 65:2220-2224 (1991)), HIV, (See Shimada et al., J. Clin. Invest., 88:1043-1047 (1991)), and avian retroviruses (See Cosset et al., J. Virology, 64:1070-1078 (1990)). In addition, various retroviral vectors are also described in U.S. Pat. Nos. 6,168,916; 6,140,111; 6,096,534; 5,985,655; 5,911,983; 4,980,286; and 4,868,116, all of which are incorporated herein by reference.

Adeno-associated virus (AAV) vectors have been successfully tested in clinical trials. See e.g., Kay et al., Nature Genet. 24:257-61 (2000). AAV is a naturally occurring defective virus that requires other viruses such as adenoviruses or herpes viruses as helper viruses. See Muzyczka, Curr. Top. Microbiol. Immun., 158:97 (1992). A recombinant AAV virus useful as a gene therapy vector is disclosed in U.S. Pat. No. 6,153,436, which is incorporated herein by reference.

Adenoviral vectors can also be useful for purposes of gene therapy in accordance with the present invention. For example, U.S. Pat. No. 6,001,816 discloses an adenoviral vector, which is used to deliver a leptin gene intravenously to a mammal to treat obesity. Other recombinant adenoviral vectors may also be used, which include those disclosed in U.S. Pat. Nos. 6,171,855; 6,140,087; 6,063,622; 6,033,908; and 5,932,210, and Rosenfeld et al., Science, 252:431-434 (1991); and Rosenfeld et al., Cell, 68:143-155 (1992).

Other useful viral vectors include recombinant hepatitis viral vectors (See, e.g., U.S. Pat. No. 5,981,274), and recombinant entomopox vectors (See, e.g., U.S. Pat. Nos. 5,721,352 and 5,753,258).

Examples of viral vectors that have already been used to express interfering RNAs within mammalian cells include retroviral vectors, lentiviral vectors, adenoviral vectors and adeno-associated viral vectors. The preparation use of these viral vectors for deliver of interfering RNA into mammalian cells were described, respectively, in papers by Barton and Medzhitov (*Proc. Natl. Acac. Sci., U.S.A.* 99:14943-14945 (2002)), Matta et al. (*Cancer Biol. Ther.* 2:206-210 (2003)), Arts et al., (*Genome Res.* (E-published Sep. 15, 2003)) and Tomar et al. (*Oncogene* 22:5712-5715 (2003)), all of which are incorporated by reference herein in their entirety.

Other non-traditional vectors may also be used for purposes of this invention. For example, International Publication No. WO 94/18834 discloses a method of delivering DNA into mammalian cells by conjugating the DNA to be delivered with a polyelectrolyte to form a complex. The complex may be microinjected into or taken up by cells.

The expression cassette encoding the chimeric RNA transcript or the DNA sequence capable of directing the transcription of a UiRNA, or a precursor thereof, or a plasmid DNA vector containing such an expression cassette, may also be introduced into cells by way of receptor-mediated endocytosis. See e.g., U.S. Pat. No. 6,090,619; Wu and Wu, J. Biol. Chem., 263:14621 (1988); Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues), which is itself coupled to an integrin receptor-binding moiety (e.g., a cyclic peptide having the sequence Arg-Gly-Asp).

Alternatively, the expression cassette encoding the chimeric RNA transcript or the DNA sequence capable of directing the transcription of a UiRNA, or a precursor thereof, or a plasmid DNA vector containing such an expression cassette can also be delivered into cells via amphiphiles. See e.g., U.S. Pat. No. 6,071,890. Typically, the exogenous expression cassette, or a vector containing it, forms a complex with the cationic amphiphile. Mammalian cells contacted with the complex can readily take it up.

The expression cassette encoding the chimeric RNA transcript or the DNA sequence capable of directing the transcription of a UiRNA, or a precursor thereof, or a DNA vector containing such an expression cassette, can be introduced into cells or tissue in vitro or in a patient for purposes of gene therapy by various methods known in the art. For example, the expression cassette alone or in a conjugated or complex form described above, or incorporated into viral or DNA vectors, may be administered directly by injection into an appropriate tissue or organ of a patient. Alternatively, catheters or like devices may be used to deliver exogenous gene sequences, complexes, or vectors into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

In addition, the expression cassette encoding a chimeric RNA transcript of the present invention, or a DNA sequence capable of directing the expression of UiRNA, or a precursor thereof, or vectors containing such expression cassettes, can be introduced into isolated cells using any known techniques such as calcium phosphate precipitation, microinjection, lipofection, electroporation, biolystics, receptor-mediated endocytosis, and the like. Cells containing the expression cassette and producing the chimeric RNA transcripts of the present invention may be selected and redelivered back to the patient by, e.g., injection or cell transplantation. The appropriate amount of cells delivered to a patient will vary with patient conditions, and desired effect, which can be determined by a skilled artisan. See e.g., U.S. Pat. Nos. 6,054,288;

6,048,524; and 6,048,729. Preferably, the cells used are autologous, i.e., cells obtained from the patient being treated.

9. Cell Models

In another aspect of the present invention, cell models are provided in which the methods of the present invention are used to manipulate the levels of expression of particular gene products using UiRNAs directed at UtRNAs located within chimeric RNA transcripts expressed within the cells. The cells can be cultured and divided, and one half treated by introduction of UiRNA, while the other half is sham treated. In this way the effects of UiRNA-induced RNAi can be evaluated. Alternatively, cells expressing the chimeric RNA transcripts of the present invention can be compared with wild type cells under conditions in which levels of expression of particular gene products are being manipulated by the introduction of UiRNAs to both groups of cells. Such cell models are useful tools for studying cellular functions and biological processes associated with particular gene products, as well as for detecting any off-target effects caused by administration or introduction of UiRNA. Such cell models are also useful tools for studying disorders and diseases associated with the overexpression or underexpression of gene products, both mutant and wild type, and can be used for testing various methods for modulating cellular functions, or for treating the diseases and disorders associated with aberrations in particular gene products or aberrations in their expression levels. Importantly, the gene products whose levels of expression are manipulated in such cell models, need not be gene products from cellular genes, but may include gene products from parasites and pathogens, including viruses.

Advantageously, human cell models in which the methods of the present invention are used to manipulate levels of gene expression are provided in accordance with the present invention. Such cell models may be established by isolating, from a patient, wild type cells, or cells having an aberrant form of one or more gene products, or cells exhibiting aberrant levels of expression of one or more gene products. The isolated cells may be cultured in vitro as a primary cell culture. Alternatively, the cells obtained from the primary cell culture or directly from the patient may be immortalized to establish a human cell line. Any methods for constructing immortalized human cell lines may be used in this respect. See generally Yeager and Reddel, Curr. Opini. Biotech., 10:465-469 (1999). For example, the human cells may be immortalized by transfection of plasmids expressing the SV40 early region genes (See e.g., Jha et al., Exp. Cell Res., 245:1-7 (1998)), introduction of the HPV E6 and E7 oncogenes (See e.g., Reznikoff et al., Genes Dev., 8:2227-2240 (1994)), and infection with Epstein-Barr virus (See e.g., Tahara et al., Oncogene, 15:1911-1920 (1997)). Alternatively, the human cells may be immortalized by recombinantly expressing the gene for the human telomerase catalytic subunit hTERT in the human cells. See Bodnar et al., Science, 279:349-352 (1998).

Alternatively, cell models may be established by isolating, from an animal or a fungus, wild type cells, or cells having an aberrant form of one or more gene products, or cells exhibiting aberrant levels of expression of one or more gene products. The isolated cells may be from any type of animal, including fungi, nematodes, insects, and pathogenic protozoa. The isolated cells may be cultured in vitro as a primary cell culture. Alternatively, the cells obtained from the primary cell culture or directly from the animal or fungi may be immortalized to establish a cell line. Any methods for constructing immortalized cell lines may be used in this respect.

Similarly, cell models may be established by isolating, from a plant, wild type cells, or cells having an aberrant form of one or more gene products, or cells exhibiting aberrant levels of expression of one or more gene products. The isolated cells may be from agriculturally important plants, such as cereal grain plants, and other crop plants, including both monocots and dicots. The isolated cells may be cultured in vitro as a primary cell culture. Alternatively, the cells obtained from the primary cell culture or directly from the plant may be immortalized to establish a plant cell line. Any methods for constructing immortalized plant cell lines may be used in this respect.

In alternative embodiments, cell models are provided by recombinantly manipulating appropriate starting cells. The starting cells may be bacterial cells, yeast cells, fungi cells, insect cells, plant cells, animal cells, and the like. Advantageously, the cells may be derived from mammals, most preferably humans. The starting cells may be obtained directly from an individual, or a primary cell culture, or preferably an immortal stable cell line. In a preferred embodiment, human embryonic stem cells or pluripotent cell lines derived from human stem cells are used as target cells. Methods for obtaining such cells are disclosed in, e.g., Shamblott, et al., Proc. Natl. Acad. Sci. USA, 95:13726-13731 (1998) and Thomson et al., Science, 282:1145-1147 (1998).

In one embodiment, a cell model is provided by recombinantly expressing a gene product from the chimeric RNA transcripts of the present invention (that also bear a UtRNA), in cells that do not normally express such a gene product. For example, cells that do not contain a particular gene product may be engineered to express that particular gene product. Alternatively, cells that express a mutant gene product may be engineered to express a corresponding non-mutant gene product from a chimeric RNA transcript that also bears a UtRNA. Simultaneously, or subsequently, UiRNAs can be introduced into these engineered cells to reduce the level of expression of the recombinantly expressed gene product. In a specific embodiment, a particular human gene product is expressed from chimeric RNA transcripts bearing UtRNAs in non-human cells. The cell model may be prepared by introducing into target cells nucleic acids containing the expression cassettes of the present invention, and expressing the encoded gene products in the target cells. For this purpose, the recombinant expression methods described in Sections 3-6 may be used. In addition, the methods for introducing nucleic acids into starting cells disclosed in the context of gene therapy in Section 8 may also be used.

In another embodiment, a cell model recombinantly expressing a particular gene product from the chimeric RNA transcripts of the present invention is provided. The overexpression of a gene product from the chimeric RNA transcripts of the present invention, that also bear UtRNAs, may be achieved by introducing into starting cells exogenous nucleic acids containing the expression cassettes of the present invention, and selecting those cells that contain the expression cassettes, produce the chimeric RNA transcripts, and over-express the encoded gene products. The expression of the gene products from the introduced exogenous nucleic acids may be transient or, preferably stable, but can be manipulated by the introduction of UiRNAs targeted to the UtRNAs in the recombinantly expressed chimeric RNA transcripts. The recombinant expression methods described in Section 3-6, and the methods for introducing nucleic acids into starting cells disclosed in the context of gene therapy in Section 8 may be used. Any cells may be employed for establishing the cell model. Preferably, human cells lacking the gene product whose expression levels are to be manipulated, or having a normal concentration of the gene product, are used as starting cells. The starting cells may be obtained directly from an individual, or a primary cell culture, or preferably a stable immortal human cell line. In a preferred embodiment, human embryonic stem cells or pluripotent cell lines derived from human stem cells are used as starting cells. Methods for obtaining such cells are disclosed in, e.g., Shamblott, et al., Proc. Natl. Acad. Sci. USA, 95:13726-13731 (1998), and Thomson et al., Science, 282:1145-1147 (1998).

9.1. Mammalian Cell Models:

In a preferred set of cell model embodiments, mammalian cells are used as target cells for expression cassettes of the present invention, and for studies in which the levels of expression of particular gene products are manipulated. The expression cassettes in these target cells direct the production of chimeric RNA transcripts bearing a UtRNA and encoding a gene product of interest. The chimeric RNA transcripts, in turn, direct the concomitant expression of the gene product of interest, however, the level of expression of the gene product of interest can be manipulated by the introduction of UiRNA designed to target the UtRNA borne by the chimeric RNA transcripts. For this purpose, virtually any mammalian cells can be used as starting cells including normal tissue cells, stable cell lines, and transformed tumor cells. Conveniently, mammalian cell lines such as CHO cells, Jurkat T cells, NIH 3T3 cells, HEK-293 cells, CV-1 cells, COS-1 cells, HeLa cells, VERO cells, MDCK cells, WI38 cells, and the like are used. Advantageously, mammalian cells that have been manipulated so as to enable the cells to conduct transitive RNAi are used.

Several mammalian expression vectors suitable for directing the expression of the chimeric RNA transcripts of the present invention are well known in the art and many are commercially available. These vectors typically contain a suitable promoter, a multiple cloning site, a transcription termination signal and a polyadenylation signal. Examples of suitable promoters for the transcription of the chimeric genes in mammalian cells include viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Inducible promoters can also be used. Suitable inducible promoters include, for example, the tetracycline responsive element (TRE) (See Gossen et al., Proc. Natl. Acad. Sci. USA, 89:5547-5551 (1992)), metallothionein IIA promoter, ecdysone-responsive promoter, and heat shock promoters. Suitable origins of replication for the replication and maintenance of the expression vectors in mammalian cells include, e.g., the Epstein Barr origin of replication in the presence of the Epstein Barr nuclear antigen (see Sugden et al., Mole. Cell. Biol., 5:410-413 (1985)) and the SV40 origin of replication in the presence of the SV40 T antigen (which is present in COS-1 and COS-7 cells) (see Margolskee et al., Mole. Cell. Biol., 8:2837 (1988)). Suitable selection markers include, but are not limited to, genes conferring resistance to neomycin, hygromycin, zeocin, and the like. Many commercially available mammalian expression vectors may be useful for the present invention, including, e.g., pCEP4, pcDNAI, pIND, pSecTag2, pVAX1, pcDNA3.1, and pBI-EGFP, and pDisplay. The vectors can be introduced into mammalian cells using any known techniques such as calcium phosphate precipitation, lipofection, electroporation, and the like.

Similarly, several mammalian transcription vectors suitable for directing the transcription of the UiRNAs, or RNAs that are processed into UiRNAs (i.e., shRNAs), of the present invention are well known in the art and many are commercially available. Preferably, these vectors contain an inducible or derepressible promoter functionally linked to the UiRNA coding sequence, such that expression of the UiRNA, or UiRNA precursor, is completely absent in the absence of an inducing or derepressing signal, but is present in the presence of an inducing or derepressing signal. In one embodiment, the transcription vectors contain nucleotide sequences that allow for integration of the vector, or some portion thereof, into the genome of target cells. In another embodiment, the vectors possess nucleotide sequences that result in tissue-specific transcription, or in the ability to manipulate the expression levels of the encoded UiRNAs, or UiRNA precursors. An example of an inducible siRNA expression system that facilitates tight control of specific gene silencing by RNAi in human cells was recently described in a paper by Chen, et al., (Cancer Res. 63:4801-4804 (2003)), which is incorporated herein by reference in its entirety.

Viral expression vectors, which permit introduction of recombinant expression cassettes into cells by viral infection, can also be used for the expression of the chimeric RNA transcripts as described above. Viral expression vectors generally known in the art include viral vectors based on adenovirus, bovine papilloma virus, murine stem cell virus (MSCV), MFG virus, and retrovirus. See Sarver, et al., Mol. Cell. Biol., 1: 486 (1981); Logan & Shenk, Proc. Natl. Acad. Sci. USA, 81:3655-3659 (1984); Mackett, et al., Proc. Natl. Acad. Sci. USA, 79:7415-7419 (1982); Mackett, et al., J. Virol., 49:857-864 (1984); Panicali, et al., Proc. Natl. Acad. Sci. USA, 79:4927-4931 (1982); Cone & Mulligan, Proc. Natl. Acad. Sci. USA, 81:6349-6353 (1984); Mann et al., Cell, 33:153-159 (1993); Pear et al., Proc. Natl. Acad. Sci. USA, 90:8392-8396 (1993); Kitamura et al., Proc. Natl. Acad. Sci. USA, 92:9146-9150 (1995); Kinsella et al., Human Gene Therapy, 7:1405-1413 (1996); Hofmann et al., Proc. Natl. Acad. Sci. USA, 93:5185-5190 (1996); Choate et al., Human Gene Therapy, 7:2247 (1996); WO 94/19478; Hawley et al., Gene Therapy, 1:136 (1994) and Rivere et al., Genetics, 92:6733 (1995), all of which are incorporated by reference.

Generally, to construct a viral vector, a chimeric gene according to the present invention can be operably linked to a suitable promoter. The promoter-chimeric gene construct is then inserted into a non-essential region of the viral vector, typically a modified viral genome. This results in a viable recombinant virus capable of expressing the fusion protein encoded by the chimeric gene in infected target cells. Once in the host cell, the recombinant virus typically is integrated into the genome of the host cell. However, recombinant bovine papilloma viruses typically replicate and remain as extrachromosomal elements.

9.2 Plant Cell and Tissue Models:

In another set of embodiments, the methods of the present invention are conducted in plant cell and tissue systems. Methods for producing chimeric RNA transcripts and expressing exogenous proteins in plant cells and tissues are well known in the art. Similarly, methods for introducing siRNAs into plant cells and tissues are well known in the art. These methods include the direct introduction of RNAs synthesized in vitro, as well as the introduction of DNA transcription cassettes and vectors that direct the in vivo production of RNAs. As described above, the RNAs introduced or expressed can be double-stranded siRNAs, or hairpin RNAs that can be processed into siRNAs in vivo, by cellular enzymes. See generally, Weissbach & Weissbach, Methods for Plant Molecular Biology, Academic Press, NY, 1988; Grierson & Corey, Plant Molecular Biology, 2d Ed., Blackie, London, 1988. An example of an tightly-regulated chemical-inducible siRNA expression system that facilitates the expression of interfering RNAs in plant cells was recently described in a paper by Guo, et al., (*Plant J.* 34:383-392 (2003)), which is incorporated herein by reference in its entirety.

Recombinant virus expression vectors based on, e.g., cauliflower mosaic virus (CaMV) or tobacco mosaic virus (TMV) can be also used. Alternatively, recombinant plasmid expression vectors such as Ti plasmid vectors and Ri plasmid vectors are also useful. The expression cassettes of the present invention directing the production of chimeric RNA transcripts encoding a gene product of interest (in the target RNA) and bearing a UtRNA can be conveniently assembled in expression vectors and placed under control of a viral promoter such as the 35S RNA and 19S RNA promoters of CaMV or the coat protein promoter of TMV, or of a plant promoter, e.g., the promoter of the small subunit of RUBISCO and heat shock promoters (e.g., soybean hsp17.5-E or hsp17.3-B promoters). Numerous other methods exist for introducing the expression cassettes and transcription cassettes of the present inventions into plant cells. The use of these methods for the practice of the instant invention will be apparent to one of skill in the art of manipulating gene expression in plant cells.

9.3 Insect Cell Models:

In addition, the methods of the present invention can also be conducted in insect cells, e.g., *Spodoptera frugiperda*, *Aedes* spp., and *Anopheles* spp. cells, using any system known in the art. For example, baculovirus-based systems can be used to introduce the expression cassettes of the present invention to *S. frugiperda* cells. Expression vectors and target cells utilizing this system are well known in the art and are generally available from various commercial vendors. For example, nucleotide sequences encoding gene products of interest functionally linked to UtRNAs can be conveniently cloned into a non-essential region (e.g., the polyhedrin gene) of an *Autographa californica* nuclear polyhedrosis virus (AcNPV) vector and placed under control of an AcNPV promoter (e.g., the polyhedrin promoter). The non-occluded recombinant viruses thus generated can be used to infect target cells such as *Spodoptera frugiperda* cells in which the chimeric genes are expressed. See, for example, U.S. Pat. No. 4,215,051.

10. Cell-Based Assays

The cell models of the present invention containing an expression cassette of the present invention are useful in screening assays for identifying compounds useful in treating diseases and disorders. In addition, they may also be used in in vitro pre-clinical assays for testing compounds, such as those identified in the screening assays of the present invention.

For example, cells may be treated with compounds to be tested and assayed for the compound's activity. A variety of parameters relevant to particularly physiological disorders or diseases may be analyzed.

11. Transgenic Animals

In another aspect of the present invention, transgenic non-human animals are created expressing chimeric RNA transcripts encoding particular gene products in their subject RNA, and bearing a UiRNA-targetable UtRNA. Animals of any species may be used to generate the transgenic animal models, including but not limited to, mice, rats, hamsters, sheep, pigs, rabbits, guinea pigs, preferably non-human primates such as monkeys, chimpanzees, baboons, and the like. Further, animals used to generate transgenic animal models may be animals that serve as vectors or reservoirs for infectious diseases that infect humans, or commercially important animals or plants. These animals may be arthropods, such as mosquitoes, fleas and ticks, or they may be from other taxonomic groups of invertebrates or vertebrates.

In one embodiment, transgenic animals are made to express chimeric RNA transcripts containing a UtRNA and a subject RNA encoding a gene product whose expression levels are to be manipulated. Over-expression of the gene products under study may be directed in a cell type or tissue that normally expresses the animal counterparts of such gene product. Consequently, the concentration of the selected gene product will be elevated to higher levels than normal. The level of expression can later be reduced, if necessary, by the introduction of UiRNAs. Alternatively, one or more gene products are expressed in tissues or cells that do not normally express such gene products, and the levels of expression of these gene products can be manipulated by the introduction of UiRNA.

To achieve over-expression in transgenic animals, the transgenic animals are made to contain exogenous nucleic acids in the form of expression cassettes that ultimately direct the production of the chimeric RNA transcripts of the present invention. These chimeric RNA transcripts, in turn, are translated to yield the gene product, or gene products, under study. Preferably, the gene products encoded in the expression cassettes are human gene products. Alternatively, the gene products can be virulence factors of pathogenic organisms, or transmission factors of a pathogenic organism's vector species. Such expression cassettes, which direct the expression of the chimeric RNA transcripts of the present invention, may include a native or non-native promoter, and preferably an inducible, or derepressible non-native promoter. If the expression of the chimeric RNA transcripts is desired to be limited to a particular tissue, an appropriate tissue-specific promoter may be used.

If a reduction of expression of the gene product under study is desired, UiRNAs targeting the UtRNA can be introduced into, or expressed within the transgenic animal bearing the expression constructs of the present invention. Methods for the introduction of in vitro synthesized UiRNAs, and for the in vivo transcription of UiRNAs are described above. Other methods of deliver of UiRNAs exist. The efficient delivery of siRNAs to organs of postnatal mice has been achieved by high pressure tail vein injection (Lewis et al., *Nat. Genet.* 32:107-108 (2002)). Lentiviral vectors directing the transcription of interfering RNA and transgenically supplied siRNA have been used successfully to affect a knockdown of gene expression in mice, as described in publications by Tiscomia et al. (*Proc. Natl. Acad. Sci. U.S.A* 100:1844-1848 (2003)) and Hasuwa et al., (FEBS Lett. 532:227-230 (2002), both of which are incorporated herein by reference in their entirety.

In a specific embodiment, the transgenic animal is a "knockout" animal wherein the endogenous gene encoding the animal orthologue of the gene product under study is knocked out. The reduced expression, or the controlled expression of the endogenous orthologue, may be achieved by knocking out the endogenous gene encoding the gene product under study, typically by homologous recombination. Alternatively, mutations that can cause reduced expression (e.g., reduced transcription and/or translation efficiency, or decreased mRNA stability) may also be introduced into the endogenous genes by homologous recombination. Genes encoding ribozymes or antisense compounds specific to the mRNAs encoding the gene product(s) under study may also be introduced into the transgenic animal. In addition, genes encoding antibodies or fragments thereof specific to the endogenous protein may also be introduced into the transgenic animal. Generally, however, the expression levels of a particular gene product under study are reduced by the introduction of, or in vivo expression of UiRNAs targeted to the UtRNAs born by the chimeric RNA transcript expressed from the expression cassettes of the present invention. In a specific embodiment, the lack of expression of the animal orthologues of the gene product under study is complemented by expression of an orthologous gene product encoded by a chimeric RNA transcript of the present invention.

In an alternate embodiment, transgenic animals are made in which the endogenous genes encoding the animal orthologues of the gene product under study are replaced with the expression cassettes of the present invention that direct the expression of chimeric RNA transcripts bearing a UtRNA, and having nucleotide sequences encoding orthologous human gene products.

In yet another embodiment, the transgenic animal of the present invention expresses specific mutant forms of the gene product under study. For this purpose, variants of the gene product under study exhibiting altered activities or properties, and the nucleic acid variants encoding such variant proteins, may be obtained by random or site-specific mutagenesis. The transgenic animal of the present invention may be made to express such protein variants by modifying the endogenous genes. Alternatively, the nucleic acid variants may be introduced exogenously into the transgenic animal genome to express the protein variants therefrom. In a specific embodiment, the exogenous nucleic acid variants are derived from orthologous human genes and the corresponding endogenous genes are knocked out.

Any techniques known in the art for making transgenic animals may be used for purposes of the present invention. For example, the transgenic animals of the present invention may be provided by methods described in, e.g., Jaenisch, *Science*, 240:1468-1474 (1988); Capecchi, et al., *Science*, 244:1288-1291 (1989); Hasty et al., *Nature*, 350:243 (1991); Shinkai et al., *Cell*, 68:855 (1992); Mombaerts et al., *Cell*, 68:869 (1992); Philpott et al., *Science*, 256:1448 (1992); Snouwaert et al., *Science*, 257:1083 (1992); Donehower et al., *Nature*, 356:215 (1992); Hogan et al., *Manipulating the Mouse Embryo; A Laboratory Manual*, 2nd edition, Cold Spring Harbor Laboratory Press, 1994; and U.S. Pat. Nos. 4,873,191; 5,800,998; 5,891,628, all of which are incorporated herein by reference. As mentioned above, methods for creating transgenic mice expressing interfering RNAs have been described in publications by Tiscomia et al. (*Proc. Natl. Acad. Sci. U.S.A.* 100:1844-1848 (2003)) and Hasuwa et al., (FEBS Lett. 532:227-230 (2002), both of which are incorporated herein by reference in their entirety.

Generally, for the purposes of the present invention, the founder lines may be established by introducing appropriate exogenous nucleic acids into, or modifying an endogenous gene in, germ lines, embryonic stem cells, embryos, or sperm which are then used in producing a transgenic animal. The gene introduction may be conducted by various methods including those described above. See also, Van der Putten et al., *Proc. Natl. Acad. Sci. USA*, 82:6148-6152 (1985); Thompson et al., *Cell*, 56:313-321 (1989); Lo, *Mol. Cell. Biol.*, 3:1803-1814 (1983); Gordon, Transgenic Animals, *Intl. Rev. Cytol.* 115:171-229 (1989); and Lavitrano et al., *Cell*, 57:717-723 (1989). In a specific embodiment, the exogenous gene is incorporated into an appropriate vector, such as those described above, and is transformed into embryonic stem (ES) cells. The transformed ES cells are then injected into a blastocyst. The blastocyst with the transformed ES cells is then implanted into a surrogate mother animal. In this manner, a chimeric founder line animal containing the exogenous nucleic acid (transgene) may be produced.

Preferably, site-specific recombination is employed to integrate the exogenous gene or expression cassette into a specific predetermined site in the animal genome, or to replace an endogenous gene or a portion thereof with the exogenous sequence. Various site-specific recombination systems may be used including those disclosed in Sauer, *Curr. Opin. Biotechnol.*, 5:521-527 (1994); Capecchi, et al., *Science*, 244:1288-1291 (1989); and Gu et al., *Science*, 265:103-106 (1994). Specifically, the Cre/lox site-specific recombination system known in the art may be conveniently used which employs the bacteriophage P1 protein Cre recombinase and its recognition sequence loxP. See Rajewsky et al., *J. Clin. Invest.*, 98:600-603 (1996); Sauer, *Methods*, 14:381-392 (1998); Gu et al., *Cell*, 73:1155-1164 (1993); Araki et al., *Proc. Natl. Acad. Sci. USA*, 92:160-164 (1995); Lakso et al., *Proc. Natl. Acad. Sci. USA*, 89:6232-6236 (1992); and Orban et al., *Proc. Natl. Acad. Sci. USA*, 89:6861-6865 (1992).

The transgenic animals of the present invention may be transgenic animals that carry a transgene in all cells or mosaic transgenic animals carrying a transgene only in certain cells, e.g., somatic cells. The transgenic animals may have a single copy or multiple copies of a particular transgene.

The founder transgenic animals thus produced may be bred to produce various offspring. For example, they can be inbred, outbred, and crossbred to establish homozygous lines, heterozygous lines, and compound homozygous or heterozygous lines.

12. Transgenic Plants

In another aspect of the present invention, transgenic plants are created expressing chimeric RNA transcripts comprising a subject RNA, which encodes a particular gene product, and a UtRNA. Plants of any species, monocot or dicot, may be used to generate the transgenic plant models. Such transgenic plant models may include, but are not limited to, *Arabadopsis thaliana*, cereal and other grain plants (e.g., maize, rice, barley and wheat), other crop plants including vegetable plants, fruit trees, tuber yielding plants (e.g., potatoes, sweet potatoes, and cassaya), tobacco, ornamental plants, and the like.

Methods for the production of transgenic plants are well known in the art. (See Jones & Sutton, eds. Plant Molecular Biology: Essential Techniques, John Wiley & Sons, Ltd., London (1997); Martinez-Zapater & Salinas, eds., *Arabidopsis* Protocols, Methods in Molecular Biology, Volume 82, Humana Press, Totowa, N.J. (1998); and Gilmartin & Bowler, eds. Molecular Plant Biology, Vol. 1, Oxford University Press, London (2002).) For example, the transgenic plants of the present invention can be created through *agrobacterium*-mediated transformation, using Ti- or Ri-plasmid into which the desired sequence is inserted. For the purposes of the present invention, the expression cassettes of the present invention that direct the expression of chimeric RNA transcripts can be inserted into the Ti- or Ri-plasmids, which can then be propagated in *agrobacterium*, and ultimately introduced into a host plant by *agrobacterium*-mediated transformation. Alternatively, the expression cassettes of the present invention can be introduced directly into plant cells by biolystics (i.e., gene gun), or into plant cell sphereoplasts by electroporation.

Regardless of the means of introduction, the introduced expression cassettes then direct the production of chimeric RNA transcripts bearing a UtRNA and a subject RNA encoding a gene product whose expression levels are to be manipulated. These chimeric RNA transcripts can then be translated to direct the overexpression of the gene product of interest. At some point in time when a reduction of expression of the encoded gene product is desired, a UiRNA can be introduced into, or synthesized within, the cells or tissues of the transgenic plant. The UiRNA, which corresponds in sequence to the UtRNAs of the chimeric RNA transcripts, induces RNAi (also known as post-transcriptional gene silencing, or PTSG in plants) by directing the degradation of the chimeric RNA transcripts. In species that exhibit transitive RNAi, secondary siRNAs produced during the initial, or primary RNAi response can target transcripts of related sequence for degradation, including transcripts produced from the plant's corresponding endogenous gene(s) (i.e., endogenous transcripts).

Particularly useful methods for producing transgenic plants that can be used for practicing the methods of the present invention have been described recently by Guo and coworkers (Guo, et al., *Plant J.* 34:383-392 (2003)). In particular, Guo and colleagues have developed a chemical-inducible Cre/loxP recombination system to trigger the expression of an intron-containing inverted-repeat inhibiting RNA plants. They have demonstrated its use in producing transgenic *Arabidopsis thaliana* and *Nicotiana benthamiana* plants, in which the in vivo transcription of inhibiting RNAs is not only induced at will, but is also stringently controlled. The methods presented can be used for the present invention, by redesigning the expression system to produce UiRNA, and preparing transgenic plants in which UiRNA production is stringently controlled but inducible at will. These transgenic plants, or tissues or cells isolated from them, can then be transfected with the expression vectors of the present invention that direct the expression of chimeric RNA transcripts bearing a subject RNA, encoding the gene product of interest, and a UtRNA. In such transfected transgenic plants, or plant tissues or cells, induction of UiRNA expression will result in silencing of the gene product encoded by the subject RNA through a primary RNAi response. During this primary RNAi response, secondary siRNAs will be produced that can affect a secondary, transitive RNAi of genes comprising regions of homologous nucleotide sequence.

13. Arrays

In another aspect of the present invention, the methods disclosed herein provide a strategy for the high throughput analysis of gene function in transfected cells, especially in transfected cells that either naturally exhibit, or are made to exhibit, transitive RNAi. In such arrays, introduction of the UiRNA initiates the RNAi-mediated destruction of the subject RNA carried on the chimeric RNA transcript expressed from the resident expression vector. Similarly, arrays of transfected or transgenic tissues or organisms are contemplated, wherein the introduction of the UiRNA to individual members of the array results in the RNAi-mediated destruction of a distinct subject RNA. In this manner, a plurality of genes can be subjected to RNA interference at the same time, through the introduction of a single UiRNA. Additionally, in order to prepare such arrays of cells, tissues, or organisms, arrays of expression vectors, or viral delivery vectors are also contemplated.

Preferably these arrays contain a plurality of addresses characterized by their association with a distinct subject RNA, whether that subject RNA is merely encoded within a naked DNA expression vector, or is being expressed within a transfected cell, tissue or organism. Preferably these arrays contain at least 2, 3, 4, 5, 6, 7, 8, 9, 10, 12, 16, 18, 24, 48, 96, 200, 500, 1000 or more distinct addresses, each characterized by an association with a distinct subject RNA.

13.1. Microarrays

In one embodiment, methods of the present invention provide for transfection microarrays. As used herein, the term "transfection microarray" refers to solid surface of at least 4 $cm^2$, upon which a plurality of spots, each with a diameter of at least 50 µm, are printed and subsequently dried or congealed in a defined regular grid pattern ("array"), where each spot initially contains at least 0.5 nl of an aqueous mixture of a nucleic acid, or nucleic acids, and a compound (e.g., gelatin) that will create a protective but semipermeable matrix around the nucleic acids when said matrix is dried or congealed, and where the individual spots within the array are separated from each other by at least 200 µm. (For examples of transfection microarrays and the methods by which they are prepared, refer to U.S. Pat. No. 6,544,790, which is incorporated by reference herein in its entirety.)

The term "transfected cell microarray," as used herein, refers to small clusters of at least 10 cells growing on the surface of a previously prepared "transfection microarray," each cluster of cells having been transfected by the nucleic acid or nucleic acids originally contained within the matrix of the spot upon which they grew. Said clusters of transfected cells may, or may not, reside within a monolayer, or contiguous "lawn" of cells in which the cells growing between transfected clusters are not themselves transfected. (For examples of transfected cell microarrays and the methods by which they are prepared, refer to U.S. Pat. No. 6,544,790, which is incorporated herein by reference.)

As used herein, the term "reverse transfection" refers to the technique whereby nucleic acids, in the form of a transfection microarray treated to facilitate transfection, are placed in a cell culture container, into which living cells are subsequently introduced and allowed to grow as a monolayer on the surface of the transfection microarray, and whereby small clusters of cells growing in direct contact with specific microarray spots take up and become transfected with the specific nucleic acid, or nucleic acids, contained within that particular microarray spot. (For details on how reverse transfections are conducted, refer to U.S. Pat. No. 6,544,790, which is incorporated herein by reference.)

Using the methods disclosed by Sabatini in U.S. Pat. No. 6,544,790, which is incorporated by reference herein in it entirety, transfected cell microarrays can be created that are suitable for inducing the silencing, or reduction of expression, of large sets of gene products using a common UiRNA. Using a coated glass slide, or other suitable solid substrate, that is printed with sets of expression vectors, each vector containing an expression cassette that directs the expression of a chimeric RNA transcript comprising an subject RNA encoding a particular gene product, and bearing a UtRNA, a living microarray of cell clusters recombinantly expressing the gene products, can be generated. Once generated, a UiRNA corresponding in sequence to the common UtRNA can be introduced to the cells of the transfected cell microarray to induce RNAi, to simultaneously reduce the expression of all gene products encoded by the set of expression vectors.

Any cell type may be used to make such arrays, as long as it can be efficiently transfected with an expression vector, and can tolerate the introduction of UiRNA to induce RNAi. For the purpose of these embodiments of the present invention, UiRNAs can be introduced into the cells of the transfected cell microarrays by any effective means. For example, UiRNAs synthesized in vitro can be introduced by transfection using lipofectamine 2000 (Invitrogen, Carlsbad, Calif.). Such in vitro-synthesized UiRNAs may be single-stranded shRNAs, or double stranded siRNA duplexes. In an alternative embodiment, the cells of the transfected cell microarrays can also be transfected with transcription vectors that direct the in vivo production of UiRNA. Alternatively, the cells can be transgenic cells capable of regulated, inducible synthesis of UiRNA upon treatment with an inducing agent. UiRNAs within such cells may take the form of double-stranded siRNA duplexes, or single stranded shRNAs.

In a preferred alternative embodiment, cells used to prepare the transfected cell microarrays of the present invention are modified in advance to contain an integrated inducible, or derepressible, expression cassette, or cassettes, that can be made to direct the synthesis of UiRNAs when provoked with a specific signal. Such cells may express either a single-stranded shRNA that is processed into a UiRNA by cellular nucleases, or two single-stranded RNAs that anneal to form a UiRNA. The advantage of such cells is that they are poised for induction of RNAi, and minimal manipulation is required for them to begin expressing the UiRNA that is targeted to the UtRNA of the chimeric RNA transcripts produced by expression vectors subsequently introduced into the cells. In particular, the methods described in a paper by Guo and coworkers (Guo, et al., *Plant J.* 34:383-392 (2003)), which is incorporated by reference herein in its entirety, can be used for the practice of the present invention in plant cell microarrays.

If the cells employed to make these transfected cell microarrays exhibit transitive RNAi, secondary siRNAs generated during the primary RNAi response (induced by the introduction of UiRNAs), will direct the silencing of endogenously expressed gene products that correspond in sequence to the recombinantly expressed gene products encoded by the chimeric RNA transcripts expressed. As indicated above, cells naturally exhibiting transitive RNAi can be used to prepare such transfected cell microarrays, as well as cells that are made to exhibit transitive RNAi.

In another set of embodiments, the living microarrays of transfected cell clusters can be used to determine or confirm what gene products are responsible for particular cellular functions, such as the detoxification of specific toxicants, or the metabolism of specific drugs. In these embodiments the set of DNAs inserted into the expression cassettes of the present invention are specifically chosen because of their suspected or known role in the phenomenon under study. Generally for such purposes, two identical microarrays of transfected cells are prepared and handled as a matched set. Within each set, one array serves as the treated experimental (test) array, while the other serves as a non-treated control. In such a matched set, specific gene products are overexpressed at defined locations or addresses within the arrays by clusters of cells. Exposure of the test array to the toxicants or drugs may occur before, after, or during the recombinant expression of the gene products under study.

In a related set of embodiments, the living microarrays of transfected cell clusters can be used to identify or confirm what pathogen or host gene products are required for infection by selected pathogenic agents, or what pathogen gene products contribute most to infectivity or pathogenicity. For example, the viral gene products required for viral infection, viral replication, or viral egress, can be identified. Alternatively, host cell gene products exploited by a pathogen to invade the host, or responsible for a host's resistance to infection, can also be identified.

Advantageously, the cells comprising living microarrays of transfected cell clusters used in such studies need not be human cells, mammalian cells or even animal cells. In fact, the cells used can be isolated from vector species that serve as reservoirs for infectious agents. For example, a living microarrays of transfected mosquito cell clusters can be employed to study what gene products are critical for the invasion or survival of a particular pathogen in mosquitoes, and the gene products tested may be host (mosquito) cell gene products, or pathogen (i.e., *Plasmodium faciparum*, dengue virus, West Nile virus) gene products.

Additionally, the living microarrays of transfected cell clusters expressing different gene products can be examined before, after, and during the introduction of UiRNA, and can be screened for clusters of cells that exhibit detectable differences from other clusters of transfected cells in the same array, or from non-transfected control cells in the same array. Alternatively, two duplicate living microarrays of transfected cell clusters can be prepared, and RNAi can be induced in one microarray by the introduction of UiRNA, while the second microarray serves as a non-treated, or sham-treated, control.

13.2. Macroarrays

Alternatively, macroarrays of cells transfected with the expression cassettes of the present invention, or even macroarrays of transgenic organisms bearing expression cassettes of the present invention, can be prepared. In such macroarrays, the cells or organisms at each separate address within the macroarray carry a unique expression cassette of the present invention, that expression cassette being capable of directing the expression of a chimeric RNA transcript of the present invention. Given such macroarrays, the methods of the present invention allow for the ready manipulation of expression levels for all of the gene products encoded in the chimeric RNA transcripts, by the introduction of the same UiRNA to all addresses within the macroarray.

Such macroarrays of transfected cells can be prepared in multi-welled plastic containers, such as standard 6 well culture plates, or 96 microwell plates, and any other readily-manipulated configurations. The transfected cells in such macroarrays may be grown in suspension, or in monolayer culture. The size and configuration of such macroarrays will be optimally chosen depending upon the number of cells required for subsequent assays, and the number of gene products under investigation. Such macroarrays can comprise 2, 3, 4, 6, 12, 18, 24, 48, 96, 120, 180, 240, 480, 960 or more clusters of transfected test cells.

For macroarrays of transgenic organisms, arrays can be produced by arranging containers suitable for the culture of such organisms, in a regular configuration with defined addresses. Such arrays may consist of test tubes arranged in a rack, or culture vessels (e.g., flower pots) arranged on a tray, and such arrays may comprise 2, 3, 4, 6, 12, 18, 24, 48, 96, 120, 180, 240, 480, 960 or more transgenic organisms.

In certain embodiments, a library of expression cassettes can be provided in which each expression cassette encodes a chimeric RNA transcript as described above comprising a subject RNA operably linked to a universal target RNA. The library should encode at least 2, 5, 6, 7, 8, 9, 10, 15, 20, 30, 40, 50, 100, 200, 500, 1,000, 5000, 10,000, 20,000, 30,000, or 50,000 different subject RNAs while all chimeric transcripts encoded by the library have a common universal target RNA (UtRNA). The subject RNAs may correspond to a collection of genes of interest, e.g., a subset of genes of an organism (e.g., virus, nematode, *drosophila*, animal or human), or substantially all genes of an organism (e.g., virus, nematode, *drosophila*, animal or human).

The expression cassettes in the library may be in expression vectors (e.g., plasmid vector, viral vector, etc.) or simply in linear strand DNA. In addition, the expression cassettes in the library can be arranged in an addressable array (e.g., on a solid support), and the identity of the subject RNA encoded by the expression cassette in each addressable spot in the array can be either known or unknown. Alternatively, the library a mixture of different expression cassettes encoding different chimeric RNA transcripts.

In one embodiment, the arrayed library can be used to produce an array of target cells as described elsewhere in the present disclosure.

In another embodiment, the library in a mixture is introduced into a plurality of cells or tissues or organisms to produce a plurality of mixed target cells for expressing therein the chimeric RNA transcripts. As such, upon inducing RNA interference with a universal interfering RNA targeting the UtRNA in the chimeric RNA transcripts, the phenotypes of each target cell exhibited under certain conditions reflect the effect of the subject RNA expressed in the target cell. Therefore, by identifying and isolating the cells exhibiting the phenotypes of interest, the identity of the subject RNA in the target cell can be determined and the function of the corresponding gene can be deciphered. Preferably, the library and the cells, tissues or organisms are contacted in a ratio such that approximately each cell receives one molecule of expression cassette. The cells can be physically separated, e.g. by spreading onto a medium support, in a similar manner to the method of cDNA library screening in bacteria or yeast host cells. The target cells are then subject to RNA interference with the universal interfering RNA described above, and also subject to certain conditions. The cells exhibiting phenotypes of interest upon RNA interference can be isolated and the expression cassette contained therein is characterized thereby associating the gene in the expression cassette with the cellular phenotype.

It is noted that in these embodiments, kits are also contemplated including the library (arrayed or disarrayed) or target cells (arrayed or disarrayed), and a universal interfering RNA targeting the universal target RNA in the library (or a vector expressing the interfering RNA), and optionally instructions for using the kits in the manner described above.

In alternative embodiments, the host cells used in making the target cells described above contain a transcription vector expressing the universal interfering RNA, preferably under certain inducing conditions. As such, the target cells are produced by introducing the expression cassettes or library of expression cassettes into the host cells. Each target cell produced in this manner contain both the transcription vector for expressing the universal interfering RNA and an expression cassette for expressing a chimeric RNA transcript having a subject RNA operably linked to a universal target RNA upon which the universal interfering RNA targets. The nucleic acid in the transcription vector encoding the universal interfering RNA can be integrated into the chromosome of the target cells. Preferably, the nucleic acid in the transcription vector or integrated in the chromosome is operably linked to an inducible promoter such that the expression of the universal interfering RNA is inducible under certain defined conditions. Any inducible promoters known in the art may be used.

Thus, the present invention also encompasses a plurality of target cells each expressing a chimeric RNA transcript that has a subject RNA operably linked to a universal target RNA, wherein at least 2, 4, 5, 6, 7, 8, 9, 10, 12, 15, 20, 32, 48, 96, 200, 500, 1,000, 5,000, 10,000 or 30,000 or more of the plurality of target cells have different subject RNAs, and wherein all of the plurality of target cells have the same universal target RNA. In addition, each of the plurality of the target cells expresses a universal interfering RNA targeting the universal target RNA. Kits comprising such plurality of target cells are also contemplated. The kits may further comprise instructions for using the kits in the various methods of the present invention.

14. Disease Applications

The methods of the present invention are useful for investigating diseases and disorders characterized by altered levels of expression of particular gene products, or involving the expression of particular virulence or transmission factors of pathogenic organisms. The methods are particularly useful in the study of diseases that either (a) infect organisms that exhibit transitive RNAi (e.g., plants), (b) require transmission through vector species that exhibit transitive RNAi, or (c) are caused by organisms that exhibit transitive RNAi (e.g., nematodes and possibly pathogenic protozoa). In each of these scenarios, the methods of the present invention can be used to manipulate the levels of expression of host gene products, such as those host gene products that are used by pathogens to recognize or invade target cells (i.e., cell surface receptors). The methods of the present invention can also be used to manipulate the levels of expression of pathogen gene products, such as gene products that, when expressed by pathogens, cause an increase in virulence of the pathogen (i.e., virulence factors). Additionally, in scenarios where a pathogen infects a transmission vector species, or intermediate host, (i.e., *Plasmodium* spp. or Arboviruses in mosquitoes), and the transmission vector or intermediate host species is responsible for transmission of the pathogen to humans, the methods of the present invention can be used to manipulate levels of expression of pathogen gene products required for the infection of the transmission vector, or transmission of the pathogen from the intermediate host to humans (i.e., "transmission factors"). When either the pathogen or intermediate host exhibits transitive RNAi, the methods of the present invention can potentially be used to reduce the expression levels of both recombinantly expressed gene products, as well as the corresponding, or homologous, endogenously expressed gene products, as described above. In such cases the methods of the present invention may provide a mechanism to block the infectious cycles of pathogenic organisms before they infect their ultimate hosts.

Advantageously, the methods of the present invention can be used to simultaneously investigate the involvement of numerous gene products, of both host and pathogen, in the course of infection by infectious disease agents. In order to conduct such investigations, microarrays of transfected cells, or even macroarrays of transgenic organisms, into which an expression cassette of the present invention has been introduced, can be prepared. The expression cassettes direct the production of chimeric RNA transcripts that comprise a subject RNA, encoding a particular gene product under study, and a UtRNA. When translated, the chimeric RNA transcripts direct the overexpression of the particular inserted gene product. When expression of the inserted gene product is to be reduced in all members of the array, the same UiRNA is introduced into, or transcribed within, the cells or organisms of the array. The UiRNA, which corresponds in sequence to the common UtRNA incorporated into the chimeric RNA transcripts, induces a primary RNAi response and causes the selective degradation of the chimeric RNA transcripts in the cells or organisms of the array. In cells or organisms that naturally exhibit transitive RNAi, or are made to exhibit transitive RNAi, secondary siRNAs produced during the primary RNAi response correspond in nucleotide sequence to regions nearby the UtRNA in the originally targeted chimeric RNA transcripts. These secondary siRNAs can induce a secondary RNAi response, and promote the degradation of the transgenically-expressed chimeric RNA transcripts, as well as endogenous transcripts bearing homologous nucleotide sequences. Consequently, introduction of UiRNAs in such cells or organisms, whether synthesized in vitro or transcribed in vivo, can lead to greatly reduced expression of the recombinantly expressed, as well as endogenously expressed, gene product under study. In essence, and with regard to the gene product under study in that particular cluster of cells or organism in the array, the result can be a silencing (functional knockdown or knockout), or at least a partial reduction of expression of a particular gene product. Consequently, the arrays described above can be used to simultaneously investigate the role of a plurality of specific gene products in all aspects of disease etiology, or in all stages in the cycle of an infectious disease including pathogen invasion, replication, egress and transmission to new hosts.

The diseases that can be studied by the methods of the present invention include genetic disorders, metabolic disorders, and infectious diseases caused by any class of pathogen, including, e.g., viruses, bacteria, fungi and protozoa. These diseases may affect humans or non-human animals, or may affect plants of any variety.

Also, as described above, the methods of the present invention can be used to study the infection of non-human intermediate hosts or transmission vector species, such as those arthropods that transmit infectious diseases to humans (e.g., mosquitoes, ticks, fleas, and the likes). For these studies, arrays of transfected arthropod (i.e., mosquito) cells may be employed.

The methods of the present invention can also be used to study the gene products involved in the infection of plants by various plant pathogens, including viruses, bacteria, fungi, nematodes, and other plant pathogens. For these studies, microarrays of transfected plant cells may be employed, or macroarrays of transgenic plants may be used.

Advantageously, since plants exhibit transitive RNAi, the methods of the present invention can be used to create and select disease- or pathogen-resistant transgenic varieties, or alternatively, can be used to develop new means to protect plants from infection by pathogens. In a particularly preferred embodiment of the present invention, a plurality of transgenic plants are prepared, in which the subject RNAs of the chimeric RNA transcripts correspond to mRNAs, or fragments of mRNAs obtained from, or expressed by a particular plant pathogen. Upon introduction of the UiRNA to these transgenic plants, preferably by the induction of in vivo transcription of the UiRNA, a primary RNAi response will be mounted. During this primary RNAi response, secondary siRNA with nucleotide sequences corresponding to regions of the subject RNA will be generated, within each plant. Since each transgenic plant expresses a different chimeric RNA transcript with a distinct subject RNA, a different set of secondary siRNAs, will made in each plant. As concentration of secondary siRNAs nears its peak, the plurality of transgenic plants can be exposed to the pathogen that served as the original source of the subject RNAs. Those transgenic plants containing certain preferred sets of secondary siRNAs should be more resistant to the pathogen than those transgenic plants containing sets of siRNAs which are ineffective at blocking infection by the pathogen. The transgenic plants that are most resistant to infection by the pathogen are selected and the subject RNA expressed within them is identified. The subject RNA thus identified corresponds to the pathogen mRNA, or mRNA fragment, that should be specifically targeted by gene-specific siRNAs expressed in subsequently produced disease-resistant, transgenic plants.

Such gene-specific siRNAs thus identified can be expected to be especially effective against infection, if the pathogen under study is a nematode. This is because nematodes have been shown to (1) take up siRNAs from the food they eat, (2) amplify the silencing signal, and (3) carry out transitive RNAi. Consequently, the methods of the present invention are particularly well-suited to identifying siRNAs that can be expressed within plant tissues that will impart resistance to attack of these tissues by nematodes. However, the methods of the present invention are clearly not limited to developing nematode-resistant plants. Indeed the subject RNAs of the chimeric RNA transcripts expressed within a plurality of transgenic can correspond in sequence to RNAs from any plant pathogen. And since siRNAs have recently been shown to mediate the interference of viral DNA accumulation in *Nicotiana tabacum* (Vanitharani et al., Proc. Natl. Acad. Sci. U.S.A. 100:9632-9636), the methods of the present invention will likely prove useful in identifying siRNAs that, when expressed within transgenic plants, impart resistance to viral infections.

Advantageously, the methods of the present invention also can be used to create transgenic plants that are resistant to infection by any number of pathogens. Specifically, once subject RNAs from several different pathogens are identified that result in the generation of secondary siRNAs effective in imparting resistance to that pathogen, transgenic plants expressing several different chimeric RNA transcripts, each with a different preferred subject RNA, but the same UtRNA can be prepared.

Importantly, RNAi has now been documented in a large number of human pathogens, including members of the family of flagellate protozoa Trypanosomatidae (Robinson & Beverly. *Mol. Biochem. Parasitol.* 128:217-228 (2003); Huynh et al., *J. Biol. Chem.* (Epub Jul. 29, 2003); Tschudi et al., *Methods* 30:304-312 (2003)), the parasitic flatworm *Schistosoma mansoni* (Boyle et al., *Mol. Biochem. Parasitol.* 128:205-215 (2003)), and the human filarial nematode parasite *Brugia malayi* (Aboobaker AND Blaxter *Mol. Biochem. Parasitol.* 129:41-51 (2003). Furthermore, stable and heritable RNAi has been achieved in the malaria vector mosquito *Anopheles stephensi* (Brown et al., *Nucleic Acids Res.* 31:e5 (2003)), and intravenous injection of siRNAs designed to silence a *Plasmodium berghei* (mouse malaria) gene into the bloodstreams of mice, affected the silencing of that gene within circulating malarial parasites (Mohmmed et al., *Biochem. Biophys Res. Commun.* 309:506-51 (2003)). These studies, and studies like these, provide support to the notion that the methods of the present invention can be useful in developing novel approaches to utilize RNAi as a means to combating the infectious diseases of humans. For example, as described above, the methods of the present invention can be used to simultaneously screen the effects of silencing a plurality of genes from human pathogens, using a single UiRNA to affect the silencing of all genes. In this fashion, specific genes from important human pathogens can be identified as viable targets for therapeutic gene-specific silencing by gene-specific interfering RNAs.

Finally, a recent report by Vanitharani and coworkers (*Proc. Natl. Acad. Sci. U.S.A.* 100:9632-9636 (2003)), which is incorporated by reference in its entirety, documents the successful siRNA-mediated suppression of gene expression in cultured plant cells, and demonstrates that siRNAs can interfere with and suppress the accumulation of a nuclear-replicated DNA virus. This report, in conjunction with the previously described chemical-regulated inducible RNAi system developed by Guo and colleagues (Guo, et al., *Plant J.* 34:383-392 (2003)), provide support to the notion that the methods of the present invention can be useful in developing novel approaches to utilize RNAi as a means to combating the infectious diseases of plants.

15. Pharmaceutical Compositions and Formulations

In another aspect of the present invention, pharmaceutical compositions are also provided containing the UiRNAs of the present invention, or RNAs that are processed into UiRNAs by cellular enzymes. The compositions are prepared as a pharmaceutical formulation suitable for administration into a patient or infected organism. Accordingly, the present invention also extends to pharmaceutical compositions, medicaments, drugs or other compositions containing one or more of the therapeutic agent in accordance with the present invention.

For example, such therapeutic agents include, but are not limited to, (1) double-stranded UiRNAs, (2) small single-stranded hairpin RNAs that are processed into UiRNAs by cellular enzymes, (3) DNA vectors that direct the transcription of double-stranded UiRNAs, (4) DNA vectors that direct the transcription of small single-stranded hairpin RNAs that are processed into UiRNAs by cellular enzymes, (5) viral vectors that direct the transcription of double-stranded UiRNAs, and (6) viral vectors that direct the transcription of small single-stranded hairpin RNAs that are processed into UiRNAs by cellular enzymes, etc.

The compositions are prepared as a pharmaceutical formulation suitable for administration into a patient or infected organism. Accordingly, the present invention also extends to pharmaceutical compositions, medicaments, drugs or other compositions containing one or more of the therapeutic agent in accordance with the present invention.

In the pharmaceutical composition, an active compound identified in accordance with the present invention can be in any pharmaceutically acceptable salt form. As used herein, the term "pharmaceutically acceptable salts" refers to the relatively non-toxic, organic or inorganic salts of the compounds of the present invention, including inorganic or organic acid addition salts of the compound. Examples of such salts include, but are not limited to, hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naphthylate salts, mesylate salts, tosylate salts, citrate salts, lactate salts, maleate salts, succinate salts, tartrate salts, fumarate salts, and the like. See, e.g., Berge, et al., J. Pharm. Sci., 66:1-19 (1977).

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacterial agents, ribonuclease inhibitors, surfactants, and antioxidants can all be included. For example, useful components include sodium chloride, acetate, citrate or phosphate buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., Annual Review of Medicine, 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., J. Clin. Psych. 45:242-247 (1984). Hydrogels can be used as a carrier for the sustained release of the active compounds. Hydrogels are generally known in the art. They are typically made by crosslinking high molecular weight biocompatible polymers into a network that swells in water to form a gel like material. Preferably, hydrogels is biodegradable or biosorbable. For purposes of this invention, hydrogels made of polyethylene glycols, collagen, or poly(glycolic-co-L-lactic acid) may be useful. See, e.g., Phillips et al., J. Pharmaceut. Sci. 73:1718-1720 (1984).

The active compounds can also be conjugated, to a water-soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, Am. J. Hosp. Pharm., 15:210-218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Generally, the toxicity profile and therapeutic efficacy of the therapeutic agents can be determined by standard pharmaceutical procedures in cell models or animal models, e.g., those provided in Section 9, 10, 11 and 13, above. As is known in the art, the LD50 represents the dose lethal to about 50% of a tested population. The ED50 is a parameter indicating the dose therapeutically effective in about 50% of a tested population. Both LD50 and ED50 can be determined in cell models and animal models. In addition, the IC50 may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers on the ED50 and/or IC50, but significantly below the LD50 obtained from cell or animal models.

It will be apparent to skilled artisans that therapeutically effective amount for each active compound to be included in a pharmaceutical composition of the present invention can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like. The amount of administration can also be adjusted as the various factors change over time.

EXAMPLES

The present invention is described in further detail by way of the following illustrative examples. However, it is not intended that the present invention be limited to the examples provided.

1. Determining What Regions of the West Nile Virus Genome Represent the Best Target Sequences for an RNAi-Based Approach to Blocking Viral Invasion, Replication, Packaging or Egress in the Mosquito Vector, *Aedes aegypti*.

West Nile virus (WNV) belongs to the family Flaviviridae; a family that comprises more than 60 viruses, many of which are important human pathogens. WNV primarily infects birds, but occasionally also infects humans and horses. Like denge virus, a closely related fellow flavivirus, WNV is transmitted to humans by the bite of the *Aedes aegypti* mosquito. Advantageously, *A. aegypti* cells (ATCC CCL-125) can be grown in culture, and are susceptible to WNV infection in vitro. WNV replicates in the cytoplasm of infected cells and has a positive strand RNA genome of about 11 kb that encodes a single polyprotein. These features make WNV a useful model system with which to study all members of the family Flaviviridae.

Recently, Caplen and colleagues at the National Institutes of Health proposed that inhibition of viral gene expression within an insect host could be used to block virus replication and subsequent transmission of the pathogen to humans. Using *Ades albopictus* C6/36 cells, and Semliki Forest virus replicons, Caplen and coworkers demonstrated that dsRNA-triggered inhibition of gene expression and viral replication could indeed be accomplished in mosquito cells (Caplen et al., *Mol. Ther.* 6:243-(2002)).

The methods of the present invention can be applied in order to determine which regions of the West Nile virus genome represent the best sequences for an RNAi-based approach to blocking viral invasion, replication, packaging or egress in the mosquito vector, *Aedes aegypti* in an array-based approach as follows.

Prepare a set of expression vectors, each containing an expression cassette that directs the expression of a chimeric RNA transcript encoding a short polypeptide representing a specific portion of about 10 to 20 amino acid residues of the West Nile virus polyprotein, and a UtRNA. Preferably the set of vectors direct the expression of a set of fusion proteins comprising polypeptides that match the sequence of the viral polyprotein at regularly spaced intervals, and a carboxyl-terminal c-myc epitope tag. The set of expression vectors are designed to direct the transcription of the encoded chimeric RNA transcripts in insect cells, using appropriate promoter sequences, etc.

Using this set of expression vectors, and the techniques of Sabatini disclosed in U.S. Pat. No. 6,544,790, prepare a matched pair of microarrays of *A. aegypti* cells (ATCC CCL-125) wherein specific clusters of cells are transfected with the various expression vector in the set. After 12-48 hours, introduce a UiRNA into the cells of one transfected cell microarray, and leave the second transfected cell microarray as an untreated control. The UiRNA will induce a primary RNAi response by targeting the UtRNA of the chimeric RNA transcripts, but secondary siRNAs corresponding to sequences in the viral genome will be generated by a secondary RNAi response. After an additional 12-48 hours, expose the cells of both transfected cell microarrays to West Nile virus suspended in the culture medium. After 12-48 hours, observe the clusters of cells in the two microarrays, and determine which cell clusters in either microarray show no signs of infection by the virus. Cell clusters that show no sign of infection in the UiRNA-treated microarray, but are infected in the untreated microarray indicate cells in which RNAi induced by specific secondary siRNAs effectively blocked viral invasion, replication, packaging or egress. The address of the cells within the microarray reveals what expression vector was used for reverse transfection of those cells, and the viral sequence contained within the expression cassette within the expression vector corresponds to a preferred siRNA target sequence. If the viral gene identity in the identified cells in not readily apparent, isolate the cells and analyze the DNA in the expression cassette to determine the identity of the gene.

2. Determining or Confirming What Drug Metabolizing Enzymes (DME) are Responsible for the Detoxification of a Toxicant.

Prepare a set of expression vectors, each containing an expression cassette that directs the expression of a chimeric RNA transcript encoding a particular DME, and a UtRNA. Preferably the set of vectors carry an inducible or derepressible promoter such that the transcription of the encoded chimeric RNA transcripts can be manipulated in human cells.

Using this set of expression vectors, and the techniques of Sabatini disclosed in U.S. Pat. No. 6,544,790, prepare a matched pair of microarrays of human cells wherein specific clusters of cells are transfected with the various expression vector in the set. After 12-48 hours, introduce a UiRNA into the cells of one transfected cell microarray, and leave the second transfected cell microarray as an untreated control. The UiRNA will induce an RNAi response by targeting the UtRNA in all of the chimeric RNA transcripts. After an additional 12-48 hours, expose the cells of both transfected cell microarrays to a toxicant suspended in the culture medium. After 12-48 hours, observe the clusters of cells in the two microarrays, and determine which cell clusters in either microarray are resistant to the toxicant. Cell clusters that are resistant to the toxicant in the untreated control array, but show signs of intoxication in the UiRNA-treated microarray, are cells containing expression vectors encoding a DME that can catalyze the detoxification of the toxicant under study.

All publications, patents and patent application publications cited above are herein incorporated by reference to the same extent as if each individual publication, patent or patent application publication was specifically and individually indicated to be incorporated by reference. The mere mentioning of the publications and patent applications does not necessarily constitute an admission that they constitute prior art to the instant invention or application.

Although the foregoing invention has been described in some detail by way of illustration and example for purposes of clarity of understanding, it will be obvious that certain changes and modifications may be practiced within the scope of the appended claims.

What is claimed is:

1. A method for altering gene expression, comprising:

providing a plurality of 10 or more target cell cultures each expressing a chimeric RNA transcript that has a subject RNA operably linked to a universal target RNA, wherein at least 10 of the plurality of 10 or more target cell cultures express chimeric RNA transcripts with different subject RNAs, and wherein all of said plurality of 10 or more target cell cultures express chimeric RNA transcripts with the same universal target RNA; and introducing into said plurality of 10 or more target cell cultures a universal interfering RNA targeting said universal target RNA, wherein said universal interfering RNA is an siRNA or shRNA.

2. The method of claim 1, wherein said step of providing said plurality of 10 or more target cell cultures comprises the steps of:

providing a plurality of 10 or more expression cassettes each directing the expression of said chimeric RNA transcript, and introducing said plurality of 10 or more expression cassettes into a plurality of 10 or more target cell cultures.

3. The method of claim 1, wherein the plurality of 10 or more target cell cultures express an endogenous equivalent of the subject RNA, and carry out transitive RNA interference.

4. The method of claim 1, wherein the step of introducing said universal interfering RNA is by way of introducing a DNA that directs the intracellular transcription of said universal interfering RNA.

5. The method of claim 1, wherein each of said target cell cultures contains an expression cassette that directs the expression of said universal interfering RNA and the step of introducing said universal interfering RNA is by way of inducing the intracellular transcription of said universal interfering RNA from said expression cassette.

6. The method of claim 1, wherein the step of introducing said universal interfering RNA comprises administering to said target cell cultures a universal interfering RNA synthesized outside of the target cells.

7. The method of claim 1, wherein said universal target RNA is located in a non-coding region of the chimeric RNA transcript.

8. The method of claim 1, wherein said chimeric RNA transcript encodes a fusion protein comprising a first amino acid sequence encoded by said subject RNA, and a second amino acid sequence encoded by said universal target RNA.

9. The method of claim 8, wherein said universal target RNA is positioned either at the 3' end of, at the 5' end of, or within, the subject RNA.

10. The method of claim 8, wherein said second amino acid sequence is a peptide selected from the group consisting of antigenic determinants, epitopes, fluorescent peptides, bioluminescent peptides and enzymes including alkaline phosphatase, horseradish peroxidase, and β-galactosidase.

11. The method of claim 1, further comprising the steps of:

detecting measurable differences in said plurality of 10 or more target cell cultures before and after introduction of said universal interfering RNA;

wherein the effects of altering gene expression are revealed through the differences in said plurality of 10 or more target cell cultures before and after introduction of said universal interfering RNA.

12. A method of altering gene expression comprising:

providing a plurality of 10 or more target cell cultures capable of transitive RNA interference, each expressing a chimeric RNA transcript that has a subject RNA operably linked to a universal target RNA, wherein at least 10 of the plurality of 10 or more target cell cultures express chimeric RNA transcripts with different subject RNAs, and wherein all of said plurality of 10 or more target cell cultures express chimeric RNA transcripts with the same universal target RNA; and introducing into said plurality of 10 or more target cell cultures a universal interfering RNA targeting said universal target RNA, wherein said universal interfering RNA is an siRNA or shRNA, and wherein said chimeric RNA transcripts are degraded by a primary RNA interference response induced by said universal interfering RNA, and homologous transcripts encoded by endogenous genes are degraded by a transitive secondary RNA interference response.

13. The method of claim 12, wherein the step of introducing said universal interfering RNA is by way of introducing a DNA that directs the intracellular transcription of said universal interfering RNA.

14. The method of claim 12, wherein each of said target cell cultures contains a transcription cassette that directs the expression of said universal interfering RNA and the step of introducing said universal interfering RNA is by way of inducing the intracellular transcription of said universal interfering RNA from said transcription cassette.

15. The method of claim 12, wherein said target cell cultures are selected from plant or nematode cell cultures.

16. A kit comprising, in a compartmentalized carrier:
a plurality of 10 or more expression vectors each comprising an expression cassette that directs the expression of a chimeric RNA transcript that has a subject RNA operably linked to a universal target RNA, wherein the expression cassettes of at least 10 of the plurality of expression vectors direct the expression of chimeric RNA transcripts with different subject RNAs, and wherein the expression cassettes of all of said plurality of expression vectors direct the expression of chimeric RNA transcripts with the same universal target RNA; and
a universal interfering RNA targeting said universal target RNA, or an interfering RNA transcription vector that directs the expression of said universal interfering RNA, wherein said universal interfering RNA is an siRNA or shRNA.

17. The kit of claim 16, wherein said plurality of expression vectors are arranged in an addressable array on a solid support.

18. A kit comprising, in a compartmentalized carrier:
a plurality of 10 or more target cell cultures each expressing a chimeric RNA transcript that has a subject RNA operably linked to a universal target RNA, wherein at least 10 of the plurality of target cell cultures express chimeric RNA transcripts with different subject RNAs, and wherein all of said plurality of target cell cultures express chimeric RNA transcripts with the same universal target RNA; and
a universal interfering RNA targeting said universal target RNA, or an expression vector that directs the expression of said universal interfering RNA,
wherein said universal interfering RNA is an siRNA or shRNA.

19. The kit of claim 18 wherein said plurality of target cell cultures is selected from plant or nematode cell cultures.

20. The kit of claim 18, wherein said plurality of target cell cultures are arranged in an addressable array on a solid support.

21. The kit of claim 16, wherein said plurality of expression vectors comprises 15 or more vectors wherein at least 15 of the expression vectors contain expression cassettes that direct the expression of chimeric RNA transcripts with different subject RNAs, and wherein all of said expression vectors contain expression cassettes that direct the expression of chimeric RNA transcripts with the same universal target RNA.

22. The kit of claim 16, wherein said plurality of expression vectors comprises 100 or more vectors wherein at least 100 of the expression vectors contain expression cassettes that direct the expression of chimeric RNA transcripts with different subject RNAs, and wherein all of said expression vectors contain expression cassettes that direct the expression of chimeric RNA transcripts with the same universal target RNA.

23. The kit of claim 16, wherein said plurality of expression vectors comprises 1000 or more vectors wherein at least 1000 of the expression vectors contain expression cassettes that direct the expression of chimeric RNA transcripts with different subject RNAs, and wherein all of said expression vectors contain expression cassettes that direct the expression of chimeric RNA transcripts with the same universal target RNA.

24. The kit of claim 18, wherein said plurality of plurality of target cell cultures comprises 12 or more target cell cultures each expressing a chimeric RNA transcript, wherein at least 12 of the target cell cultures express chimeric RNA transcripts with different subject RNAs, and wherein all of said target cell cultures express chimeric RNA transcripts with the same universal target RNA.

25. The kit of claim 18, wherein said plurality of plurality of target cell cultures comprises 96 or more target cell cultures each expressing a chimeric RNA transcript, wherein at least 96 of the target cell cultures express chimeric RNA transcripts with different subject RNAs, and wherein all of said target cell cultures express chimeric RNA transcripts with the same universal target RNA.

26. The kit of claim 18, wherein said plurality of plurality of target cell cultures comprises 1000 or more target cell cultures each expressing a chimeric RNA transcript, wherein at least 1000 of the target cell cultures express chimeric RNA transcripts with different subject RNAs, and wherein all of said target cell cultures express chimeric RNA transcripts with the same universal target RNA.

27. The kit of claim 16 wherein said chimeric RNA transcript encodes a fusion protein comprising a first amino acid sequence encoded by said subject RNA, and a second amino acid sequence encoded by said universal target RNA.

28. The kit of claim 27 wherein said second amino acid sequence is a detectable peptide tag.

29. The kit of claim 28 wherein said detectable peptide tag is fused to the carboxyl-terminus of said first amino acid sequence.

30. The kit of claim 28 wherein said detectable peptide tag is either an epitope tag selected from influenza virus hemagglutinin, Simian Virus 5 (V5), polyhistidine, or c-myc; an enzymatic tag selected from alkaline phosphatase, horseradish peroxidase, or β-galactosidase; or a fluorescent peptide.

31. The kit of claim 18 wherein said chimeric RNA transcript encodes a fusion protein comprising a first amino acid sequence encoded by said subject RNA, and a second amino acid sequence encoded by said universal target RNA.

32. The kit of claim 31 wherein said second amino acid sequence is a detectable peptide tag.

33. The kit of claim 32 wherein said detectable peptide tag is fused to the carboxyl-terminus of said first amino acid sequence.

34. The kit of claim 32 wherein said detectable peptide tag is either an epitope tag selected from influenza virus hemagglutinin, Simian Virus 5 (V5), polyhistidine, or c-myc; or an enzymatic tag selected from alkaline phosphatase, horseradish peroxidase, or β-galactosidase; or a fluorescent peptide.

* * * * *